US008338178B2

(12) United States Patent
Hyde et al.

(10) Patent No.: US 8,338,178 B2
(45) Date of Patent: Dec. 25, 2012

(54) MITOCHONDRIAL ENHANCEMENT OF CELLS

(75) Inventors: Roderick A. Hyde, Redmond, WA (US);
Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 57 days.

(21) Appl. No.: 12/925,849

(22) Filed: Oct. 28, 2010

(65) Prior Publication Data

US 2012/0107937 A1    May 3, 2012

Related U.S. Application Data

(63) Continuation-in-part of application No. 12/925,850, filed on Oct. 28, 2010.

(51) Int. Cl.
*C12N 15/00*    (2006.01)
*C12N 5/00*    (2006.01)
*C12N 13/00*    (2006.01)

(52) U.S. Cl. ............... 435/440; 435/410; 435/173.1

(58) Field of Classification Search .................. None
See application file for complete search history.

(56) References Cited

U.S. PATENT DOCUMENTS

| | | | |
|---|---|---|---|
| 5,888,498 A | 3/1999 | Davis et al. | |
| 6,300,543 B1 | 10/2001 | Cass et al. | |
| 2003/0159167 A1 | 8/2003 | Hayashi | |
| 2004/0192627 A1 | 9/2004 | Weissig et al. | |
| 2006/0026694 A1 | 2/2006 | Lanza et al. | |
| 2006/0199778 A1 | 9/2006 | Ellis-Behnke et al. | |
| 2006/0236416 A1 | 10/2006 | Nagao et al. | |
| 2007/0128726 A1 | 6/2007 | Koob et al. | |
| 2008/0057039 A1 | 3/2008 | Newell Rogers et al. | |
| 2008/0090266 A1 | 4/2008 | Hattori et al. | |
| 2008/0182243 A1 | 7/2008 | Callahan et al. | |

OTHER PUBLICATIONS

Allen et al.; "Comparisons Among Two Fertile and Three Male-Sterile Mitochondrial Genomes of Maize"; Genetics; Oct. 2007; pp. 1173-1192; vol. 177; Genetics Society of America.
Altschul et al.; "Basic Local Alignment Search Tool"; J. Mol. Biol.; 1990; pp. 403-410; vol. 215; Academic Press Limited.
Bacman et al.; "Transmitochondrial Technology in Animal Cells"; Methods in Cell Biology; Chapter 25; 2007; pp. 503-524; vol. 80 ; Elsevier Inc.
Carpentieri et al.; "Respiratory and Calcium Transport Functions of Mitochondria Isolated from Normal and Transformed Human Lymphocytes"; Cancer Research; Feb. 1980; pp. 221-224; vol. 40.
Choo-Kang et al.; "Defining the Importance of Mitochondrial Gene Defects in Maternally Inherited Diabetes by Sequencing the Entire Mitochondrial Genome"; Diabetes; Jul. 2002; pp. 2317-2320; vol. 51.

Corpet; Florence; "Multiple sequence alignment with hierarchical clustering"; Nucleic Acids Research; 1988; pp. 10881-10890; vol. 16, No. 22.
Cummins, James M.; "Mitochondria: potential roles in embryogenesis and embryogenesis and nucleocytoplasmic transfer"; Human Reproduction Update; 2001; pp. 217-228; vol. 7, No. 2; European Society of Human Reproduction and Embryology.
Dahan, Maxime; "From analog to digital: exploring cell dynamics with single quantum dots"; Histochemistry and Cell Biology; May 2006; Abstract; one page; pp. 451-456; vol. 125, No. 5.
Dib et al.; "Safety and Feasibility of Autologous Myoblast Transplantation in Patients With Ischemic Cardiomyopathy Four-Year Follow-Up"; Circulation; 2005; pp. 1748-1755; vol. 112; American Heart Association, Inc.
Dumas et al.; "Gametes and Fertilization: Maize as a Model System for Experimental Embryogenesis in Flowering Plants"; The Plant Cell; Oct. 1993; pp. 1337-1348; vol. 5; American Society of Plant Physiologists.
Hecht et al.; "The Arabidopsis Somatic Embryogenesis Receptor Kinase 1 Gene Is Expressed in Developing Ovules and Embryos and Enhances Embryogenic Competence in Culture"; Plant Physiology; Nov. 2001; pp. 803-816 plus correction page; vol. 127; American Society of Plant Biologists.
Inoue et al.; "Isolation of Mitochondrial DNA-less Mouse Cell Lines and Their Application for Trapping Mouse Synaptosomal Mitochondrial DNA with Deletion Mutations"; The Journal of Biological Chemistry; Jun. 13, 1997; pp. 15510-15515; vol. 272, No. 24; The American Society for Biochemistry and Molecular Biology, Inc.
Kagawa et al.; "Gene therapy of mitochondrial diseases using human cytoplasts"; Gene Therapy; 1997; pp. 6-10; vol. 4; Stockton Press.
Keeney et al.; "ALS spinal neurons show varied and reduced mtDNA gene copy numbers and increased mtDNA gene deletions"; Molecular Neurodegeneration; 2010; pp. 1-9; vol. 5, No. 21; BioMed Central Ltd.
Keeney et al.; "Mitochondrial gene therapy augments mitochondrial physiology in a Parkinson's disease cell model"; Hum. Gene Ther.; Aug. 2009; Abstract; one page; pp. 897-907; vol. 20, No. 8.
Kubo et al.; "Angiosperm mitochondrial genomes and mutations"; Mitochondrion; Jan. 2008; Abstract; two pages; pp. 5-14; vol. 8, Issue 1.
Levy et al.; "Cytoplasmic transfer in oocytes: biochemical aspects"; Human Reproduction Update; 2004; pp. 241-250; vol. 10, No. 3; European Society of Human Reproduction and Embryology.
MacKenzie et al.; "Higher Plant Mitochondria"; The Plant Cell; Apr. 1999; pp. 571-585; vol. 11; American Society of Plant Physiologists.
Marin-Garcia et al.; "Mitochondrial-nuclear Cross-talk in the Aging and Failing Heart"; Cardiovascular Drugs and Therapy; Dec. 2006; Abstract; one page; pp. 477-491; vol. 20, No. 6.
Mazzini et al.; "Mesenchymal stem cell transplantation in amyotrophic lateral sclerosis: A Phase I clinical trial"; Exp. Neurol; May 2010; Abstract; one page; pp. 229-237; vol. 223, No. 1.

(Continued)

*Primary Examiner* — Doug Schultz

(57) ABSTRACT

Certain embodiments disclosed herein include, but are not limited to, at least one of compositions, methods, devices, systems, kits, or products regarding rejuvenation or preservation of stem cells. Certain embodiments disclosed herein include, but are not limited to, methods of modifying stem cells, or methods of administering modified stem cells to at least one biological tissue.

10 Claims, 13 Drawing Sheets

OTHER PUBLICATIONS

Muratovska et al.; "Targeting peptide nucleic acid (PNA) oligomers to mitochondria within cells by conjugation to lipophilic cations: implications for mitochondrial DNA replication, expression and disease"; Nucleic Acids Research; 2001; pp. 1852-1863; vol. 29, No. 9; Oxford University Press.

Opie et al.; "Surgical and catheter delivery of autologous myoblasts in patients with congestive heart failure"; Nat. Clin. Pract. Cardiovasc. Med.; Mar. 2006; Abstract; one page; Suppl 1; pp. S42-S45; vol. 3.

Pittenger et al.; "Multilineage Potential of Adult Human Mesenchymal Stem Cells"; Science; Apr. 2, 1999; Abstract; one page; pp. 143-147; vol. 284, No. 5411.

Poyton et al.; "Crosstalk between nuclear and mitochondrial genomes"; Annu. Rev. Biochem.; 1996; Abstract; one page; pp. 563-607; vol. 65.

Pye et al.; "Production of transmitochondrial cybrids containing naturally occurring pathogenic mtDNA variants"; Nucleic Acids Research; 2006; pp. 1-8; vol. 34, No. 13.

Ruiz-Pesini et al.; "An enhanced MITOMAP with a global mtDNA mutational phylogeny"; Nucleic Acids Research; 2007; pp. D823-D828; vol. 35.

Silvagno et al.; "Mitochondrial Localization of Vitamin D Receptor in Human Platelets and Differentiated Megakaryocytes"; PLoS ONE; Jan. 2010; pp. 1-8; vol. 5, Issue 1.

Spikings et al.; "Transmission of mitochondrial DNA following assisted reproduction and nuclear transfer"; Human Reproduction Update; 2006; pp. 401-415; vol. 12, No. 4; Oxford University Press on behalf of the European Society of Human Reproduction and Embryology.

Yoon et al.; "Efficient cloning and engineering of entire mitochondrial genomes in *Escherichia coli* and transfer into transcriptionally active mitochondria"; Nucleic Acids Research; 2003; pp. 1407-1415; vol. 31, No. 5; Oxford University Press.

FIG. 4

400 the at least one exogenous cellular component includes at least one of exogenous mitochondria, exogenous mitochondrial DNA, exogenous cell nucleus, exogenous DNA from the nucleus, or exogenous nucleocytoplasm 410 wherein receiving on a computer-readable medium a first input associated with a first possible dataset, comprises: receiving the first input associated with the first possible dataset, the first input including data representative of one or more of the one or more mitochondrial DNA characteristics 420 receiving on a computer-readable medium a first input associated with a first possible dataset, comprises: receiving the first input associated with the first possible dataset, the first input including data representative of one or more of the one or more mitochondrial DNA characteristics, including at least one of a genetic attribute, single nucleotide polymorphism, haplotype, allelic marker, allele, disease marker, genetic abnormality, genetic disease, genetic mutation, inversion, deletion, duplication, recombination, nucleic acid sequence, gene, protein coding sequence, intron, exon, regulatory sequence, intergenic sequence, mitochondrial nucleic acid sequence, mitochondria, methylation pattern, or epigenetic element 430 receiving on a computer-readable medium a first input associated with a first possible dataset comprises: receiving the first input associated with the first possible dataset, the first input including data representative of one or more mitochondrial DNA characteristics of at least one of a genome, or nucleic acid 440 receiving on a computer-readable medium a first input associated with a first possible dataset comprises: receiving a first data entry associated with the first possible dataset 450 receiving on a computer-readable medium a first input associated with a first possible dataset comprises: receiving a first data entry associated with the first possible dataset, the first data entry including data representative of one or more of the one or more mitochondrial DNA characteristics 460 receiving on a computer-readable medium a first data entry associated with a first possible dataset, the first data entry including data representative of one or more of the at least one mitochondrial DNA characteristics, comprises: receiving on a computer-readable medium a first data entry associated with the first possible dataset, the first data entry including data representative of one or more of the one or more mitochondrial DNA characteristics, including at least one of a genetic attribute, single nucleotide polymorphism, haplotype, allelic marker, allele, disease marker, genetic abnormality, genetic disease, chromosomal abnormality, genetic mutation, intron, exon, deletion, duplication, recombination, chromosome, nucleic acid sequence, gene, protein coding sequence, intron, exon, regulatory sequence, intergenic sequence, mitochondrial nucleic acid sequence, mitochondria, telomere, telomere length, centromere repeat, telomere length, centromere repeat, centromere, methylation pattern, or epigenetic element

FIG. 5

| |
|---|
| 500 receiving on a computer-readable medium a first input associated with a first possible dataset comprises: receiving on a computer-readable medium a first data entry from a graphical user interface |
| 510 receiving on a computer-readable medium a first input associated with a first possible dataset comprises: receiving on a computer-readable medium a first data entry from at least one submission element of a graphical user interface |
| 520 receiving on a computer-readable medium a first input associated with a first possible dataset comprises: receiving on a computer-readable medium a first data entry at least partially identifying one or more elements of the first possible dataset |
| 530 receiving on a computer-readable medium a first data entry at least partially identifying one or more elements of the first possible dataset comprises: receiving on a computer-readable medium the first data entry at least partially identifying the one or more elements of the first possible dataset, one or more of the one or more elements including data representative of one or more genetic characteristics |
| 540 receiving on a computer-readable medium a first data entry at least partially identifying the one or more elements of the first possible dataset comprises: receiving on a computer-readable medium the first data entry at least partially identifying one or more elements of the first possible dataset, one or more of the one or more elements including data representative of one or more of the at least one of a genome, chromosome, or nucleic acid |
| 550 receiving on a computer-readable medium a first data entry at least partially identifying one or more elements of the first possible dataset comprises: receiving on a computer-readable medium the first data entry at least partially identifying the one or more elements of the first possible dataset, one or more of the one or more elements including data representative of at least one biological tissue or biological cell |
| 560 the at least one biological cell includes one of a blood cell, muscle cell, nerve cell, fibroblast, adipose cell, stem cell, pluripotent cell, epithelial cell, skin cell, liver cell, spleen cell, oocyte, Sertoli cell, neoplastic cell, hematopoietic stem cell, lymphocyte, thymocyte, neuronal stem cell, sperm cell, retinal cell, pancreatic cell, osteoclast, osteoblast, myocyte, embryonic stem cell, fetal cell, embryonic cell, keratinocyte, mucosal cell, mesenchymal stem cell, T cell, B cell, memory T cell, memory B cell, antigen presenting cell, lymphocyte, thymocyte, meristematic cell, parenchyma cell, collenchymas cell, sclerenchyma cell, or other cell |

FIG. 6

600 accessing the first possible dataset in response to the first input 610 accessing the first possible dataset in response to the first input comprises: accessing the first possible dataset in response to the first input, the first input including data representative of one or more of the at least one mitochondrial genetic characteristic 620 accessing the first possible dataset in response to the first input comprises: accessing the first possible dataset from within a first database associated with a plurality of genetic characteristics 630 accessing the first possible dataset in response to the first input comprises: accessing the first possible dataset by associating one or more of the at least one mitochondrial genetic characteristic with one or more elements of the first possible dataset 640 accessing the first possible dataset in response to the first input comprises: accessing the first possible dataset using a database management system engine configured to query a first database to retrieve the first possible dataset therefrom 650 accessing the first possible dataset in response to the first input comprises: accessing the first possible dataset by corresponding one or more of the at least one mitochondrial genetic characteristic with one or more elements of the first possible dataset 660 accessing the first possible dataset by corresponding one or more of the one or more mitochondrial DNA characteristics with one or more elements of the first possible dataset comprises: accessing the first possible dataset by corresponding one or more of the one or more mitochondrial DNA characteristics including at least one of a genetic attribute, single nucleotide polymorphism, haplotype, allelic marker, allele, disease marker, genetic abnormality, genetic disease, chromosomal abnormality, genetic mutation, intron, exon, regulatory sequence, intergenic sequence, mitochondrial nucleic acid sequence, gene, protein coding sequence, intron, exon, regulatory sequence, intergenic sequence, mitochondrial nucleic acid sequence, mitochondria, telomere, telomere repeat, telomere length, centromere repeat, centromere, methylation pattern, or epigenetic element with the one or more elements of the first possible dataset

FIG. 7

700 accessing the first possible dataset in response to the first input comprises: accessing the first possible dataset as being associated with one or more of the one or more mitochondrial DNA characteristics, based on one or more characterizations stored in association with one or more elements of the first possible dataset 710 accessing the first possible dataset in response to the first input comprises: accessing the first possible dataset as being associated with one or more of the one or more mitochondrial DNA characteristics, based on one or more characterizations stored in association with one or more elements of the first possible dataset, the one or more elements including one or more genetic characteristics 720 receiving on a computer-readable medium a first input associated with a first possible dataset comprises: receiving on a computer-readable medium a first request associated with the first possible dataset 730 receiving on a computer-readable medium a first input associated with a first possible dataset comprises: receiving on a computer-readable medium a first request associated with the first possible dataset, the first request selecting one or more of the one or more mitochondrial DNA characteristics 740 receiving a first input associated with a first possible dataset comprises: receiving on a computer-readable medium a first request from a graphical user interface 750 receiving on a computer-readable medium a first input associated with a first possible dataset comprises: receiving on a computer-readable medium a first request from at least one submission element of a graphical user interface 760 receiving on a computer-readable medium a first input associated with a first possible dataset comprises: receiving on a computer readable medium a first request, the first request at least partially identifying one or more elements of the first possible dataset 770 receiving on a computer-readable medium a first input associated with a first possible dataset comprises: receiving on a computer-readable medium a first request, the first request selecting one or more elements of the first possible dataset 780 receiving on a computer-readable medium a first input associated with a first possible dataset comprises: receiving on a computer-readable medium a first request, the first request providing instructions at least partially identifying one or more of the one or more mitochondrial DNA characteristics

FIG. 8

800 receiving on a computer-readable medium a first input associated with a first possible dataset comprises: receiving on a computer-readable medium a first input, the first request providing instructions for determining one or more of the one or more mitochondrial DNA characteristics 810 receiving on a computer-readable medium a first input associated with a first possible dataset comprises: accessing the first possible dataset in response to a first request, the first request specifying one or more of the one or more mitochondrial DNA characteristics and at least one other instruction 820 the method further comprises: generating with a computer-recordable medium, the first possible dataset in response to the first input 830 generating with a computer-recordable medium, the first possible dataset in response to the first input comprises: generating with a computer-recordable medium, the first possible dataset in response to the first input, the first input including data representative of one or more of the one or more mitochondrial DNA characteristics 840 generating with a computer-recordable medium the first possible dataset in response to the first input comprises: generating with a computer-recordable medium, the first possible dataset from within a first database associated with a plurality of genetic characteristics 850 generating with a computer-recordable medium, the first possible dataset in response to the first input comprises: generating with a computer-recordable medium, the first possible dataset by associating one or more of the one or more mitochondrial DNA characteristics with one or more elements of the first possible dataset 860 generating with a computer-recordable medium, the first possible dataset in response to the first input comprises: generating with a computer-recordable medium the first possible dataset using a database management system engine configured to query a first database to retrieve the first possible dataset therefrom

FIG. 9

| |
|---|
| 900 generating with a computer-recordable medium, the first possible dataset in response to the first input comprises: generating with a computer-recordable medium, the first possible dataset by corresponding one or more of the one or more mitochondrial DNA characteristics with one or more elements of the first possible dataset |

| |
|---|
| 910 one or more instructions for comparing information regarding at least one aspect of at least one therapeutic administration of at least one frozen particle therapeutic composition to at least one biological tissue of at least one subject, and information regarding at least one clinical outcome following receipt by the at least one subject of at least one frozen particle therapeutic composition |

| |
|---|
| 920 receiving on a computer-readable medium the first input associated with a first possible dataset comprises: receiving on a computer-readable medium a first request associated with the first possible dataset, the first request selecting one or more of the one or more mitochondrial DNA characteristics |

| |
|---|
| 930 receiving on a computer-readable medium a first input associated with a first possible dataset comprises: receiving on a computer-readable medium a first request from at least one submission element of a graphical user interface |

| |
|---|
| 940 receiving on a computer-readable medium a first input associated with a first possible dataset comprises: receiving on a computer-readable medium a first request, the first request at least partially identifying one or more elements of the first possible dataset |

| |
|---|
| 950 receiving on a computer-readable medium a first input associated with a first possible dataset comprises: receiving on a computer-readable medium a first request, the first request selecting one or more elements of the first possible dataset |

| |
|---|
| 960 receiving on a computer-readable medium a first input associated with a first possible dataset comprises: receiving on a computer-readable medium a first request, the first request providing instructions at least partially identifying one or more of the one or more mitochondrial DNA characteristics |

| |
|---|
| 970 receiving on a computer-readable medium a first input associated with a first possible dataset comprises: receiving on a computer-readable medium a first request, the first request providing instructions for determining one or more of the one or more mitochondrial characteristics |

FIG. 10

1000 receiving on a computer-readable medium a first input associated with a first possible dataset comprises: receiving on a computer-readable medium a first request associated with the first possible dataset; and generating with a computer-recordable medium the first possible dataset in response to the first request, the first request specifying one or more of the one or more mitochondrial DNA characteristics and at least one other instruction 1010 receiving on a computer-readable medium a first input associated with a first possible dataset comprises: receiving on a computer-readable medium a first request, the first request specifying one or more of the one or more mitochondrial DNA characteristics; and generating with a computer-recordable medium the first possible dataset in response to the first request at least partially by performing an analysis of one or more of the one or more mitochondrial DNA characteristics 1020 the method further comprises determining a graphical illustration of the first possible dataset 1030 determining a graphical illustration of the first possible dataset comprises: determining the graphical illustration for inclusion in a display element of a graphical user interface 1040 determining a graphical illustration of the first possible dataset comprises: performing an analysis of one or more elements of the first possible dataset to determine a first possible outcome; and determining the graphical illustration based at least in part on the analysis 1050 determining a graphical illustration of the first possible dataset comprises: performing an analysis of one or more elements of the first possible dataset to determine a first possible outcome, the first possible outcome including one or more of a possible risk, a possible result, a possible consequence, a likelihood of success, or a cost; and determining the graphical illustration based on the analysis 1060 determining a graphical illustration of the possible dataset comprises: performing an analysis of one or more elements of the first possible dataset to determine a first possible outcome, the first possible outcome including one or more of a predicted risk, predicted result, predicted consequence; and determining the graphical illustration based on the analysis 1070 determining the graphical illustration of the first possible dataset comprises: performing an analysis of one or more elements of the first possible dataset to determine a first possible outcome, the first possible outcome including one or more of a predicted risk, predicted result, or predicted consequence; and determining the graphical illustration including one or more of the one or more mitochondrial characteristics in association with a visual indicator related to the first possible outcome

FIG. 11

1100 determining a graphical illustration of the first possible dataset comprises: determining a correlation between a first possible outcome and a type or characteristic of a visual indicator used in the graphical illustration to represent the first possible outcome 1110 the at least one exogenous cellular component is derived from a maternally genetically related cell

FIG. 12

| 1200 computer program product |
|---|
| 1210 a computer-recordable medium bearing at least one of one or more instructions for receiving a first input associated with a first possible dataset, the first possible dataset including data representative of one or more mitochondrial DNA characteristics; wherein at least one of the one or more mitochondrial DNA characteristics is a genetic characteristic; and one or more instructions for determining parameters for selecting one or more characteristics based on one or more of a mitochondria, mitochondrial DNA, cell nucleus, or nucleocytoplasm, from the first possible dataset |
| 1220 the computer program product further comprises one or more instructions for accessing the first possible dataset in response to the first input |
| 1230 the computer program product further comprises one or more instructions for generating the first possible dataset in response to the first input |
| 1240 the computer program product further comprises: one or more instructions for determining a graphical illustration of the first possible dataset |
| 1250 the computer-recordable medium medium includes a computer-readable medium |
| 1260 the computer-recordable medium includes a recordable medium |
| 1270 the computer-recordable medium includes a communications medium |

FIG. 13

1300 A system comprises 1310 a computing device; and instructions that when executed on the computing device cause the computing device to receive a first input associated with a first possible dataset, the first possible dataset including data representative of one or more mitochondrial DNA characteristics; wherein at least one of the one or more mitochondrial DNA characteristics is a genetic characteristic; and instructions that when executed on the computing device cause the computing device to determine parameters for selecting at least one exogenous cellular component for transfer to a eukaryotic cell based on the first possible dataset 1320 the at least one exogenous cellular component includes at least one of exogenous mitochondria, exogenous mitochondrial DNA, exogenous cell nucleus, or exogenous nucleocytoplasm 1330 the at least one exogenous cellular component is derived from a maternally genetically related cell 1340 further comprising instructions that when executed on the computing device cause the computing device to access the first possible dataset in response to the first input 1350 further comprising instructions that when executed on the computing device cause the computing device to generate the first possible dataset in response to the first input. In an embodiment, the system further comprises: instructions that when executed on the computing device cause the computing device to determine a graphical illustration of the first possible dataset 1360 the computing device comprises: one or more of a desktop computer, workstation computer, computing system, cluster of processors, networked computer, tablet personal computer, laptop computer, or personal digital assistant 1370 the computing device is operable to communicate with a database to access the first possible dataset 1380 the computing device is operable to communicate with an apparatus configured to select the at least one exogenous cellular component for transfer into the eukaryotic cell

MITOCHONDRIAL ENHANCEMENT OF CELLS

CROSS-REFERENCE TO RELATED APPLICATIONS

The present application is related to and claims the benefit of the earliest available effective filing date(s) from the following listed application(s) (the "Related applications") (e.g., claims earliest available priority dates for other than provisional patent applications or claims benefits under 35 USC §119(e) for provisional patent applications, for any and all parent, grandparent, great-grandparent, etc. applications of the Related application(s)). All subject matter of the Related applications and of any and all parent, grandparent, great-grandparent, etc. applications of the Related applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/925,850, entitled MITOCHONDRIAL ENHANCEMENT OF CELLS, naming Roderick A. Hyde and Lowell L. Wood, Jr. as inventors, filed 28 Oct. 2010, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related applications and of any and all parent, grandparent, great-grandparent, etc. applications of the Related applications is incorporated herein by reference to the extent such subject matter is not inconsistent herewith.

SUMMARY

Disclosed herein include embodiments relating to compositions, methods, delivery devices, computer systems, program products, and computer-implemented methods related to modified stem cells.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 4 illustrates a partial view of a particular embodiment of the method of FIG. 3.

FIG. 5 illustrates a partial view of a particular embodiment of the method of FIG. 3.

FIG. 6 illustrates a partial view of a particular embodiment of the method of FIG. 3.

FIG. 7 illustrates a partial view of a particular embodiment of the method of FIG. 3.

FIG. 8 illustrates a partial view of a particular embodiment of the method of FIG. 3.

FIG. 9 illustrates a partial view of a particular embodiment of the method of FIG. 3.

FIG. 10 illustrates a partial view of a particular embodiment of the method of FIG. 3.

FIG. 11 illustrates a partial view of a particular embodiment of the method of FIG. 3.

FIG. 12 illustrates a partial view of a particular embodiment of a computer program product.

FIG. 13 illustrates a partial view of a particular embodiment of a system.

DETAILED DESCRIPTION

Figure 1:
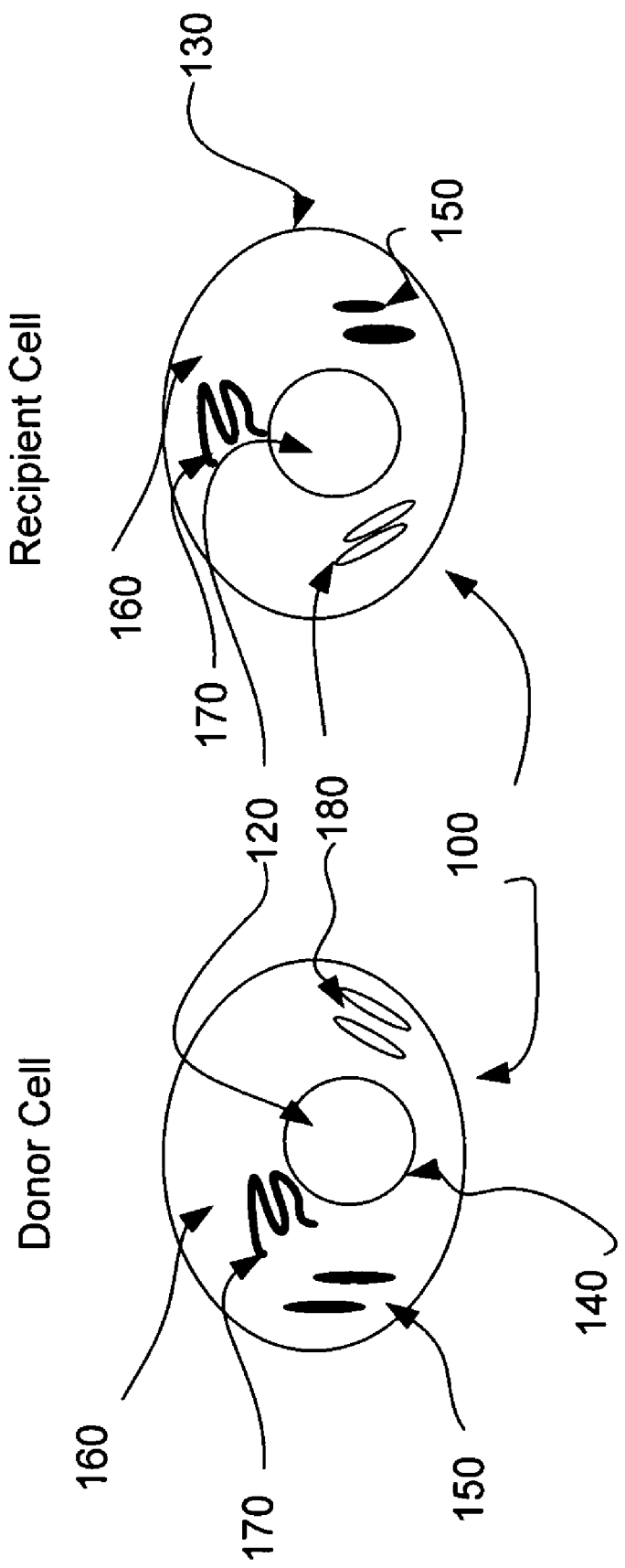
FIG. 1 illustrates a partial view of an example of a biological cell, including various components.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Certain aspects described herein relate to modifying a eukaryotic cell by providing at least one exogenous cellular component. In an embodiment, the exogenous cellular component includes at least one of an exogenous mitochondria, exogenous mitochondrial DNA, DNA of the cell nucleus, or exogenous cell nucleus to the eukaryotic cell. In an embodiment, at least one of the exogenous mitochondria, exogenous mitochondrial DNA, or exogenous cell nucleus is derived from a maternally genetically related cell.

Mitochondria are controlled by a dual genome system (particularly in humans) with cooperation between endogenous mitochondrial genes and mitochondrial genes translocated to the nucleus over the course of evolution. See, for example, Cummins, Human Rep. Update vol. 7, no. 2, pp. 217-228 (2001), which is incorporated herein by reference. Mitochondria likely play a role in aging, apoptosis, metabolism, and many diseases. The mitochondrial genome is highly compact, with little tolerance for mutations. Id. Thus, the ability to construct cells, cell systems, or animal embryos with maternally genetically related mitochondria, mitochondrial DNA, or cell nucleus, will provide powerful tools for biological tissue generation, regeneration, and alleviation of a subject from diseases.

The function of mitochondria by both genes of the nucleus and mitochondrial genes can result in conflict, under certain conditions. Id. For example, genome imprinting occurs where certain genes influencing placental and embryonic development are expressed or suppressed according to whether they pass through paternal or maternal gametogenesis. Id.

The complete mitochondrial sequence is known for more than 58 chordate and 29 non-chordate species. Id. The genome is generally a closed circular molecule with little redundancy, although linear forms with telomere-like terminations are known. Id. Mitochondrial DNA is generally tightly linked to the electron transport system and is vulnerable to damage since certain components mutate up to 100 times more rapidly than DNA of the cell nucleus. Id.

It has been published that cell lines can be constructed devoid of endogenous mitochondrial DNA (mtDNA), and re-populated with xenogenic mitochondrial lineages, which demonstrates that survival of mitochondrial genotypes is dependent on the nucleus background. Id. Furthermore, it has been published that rat mtDNA can restore translation but not respiration in mtDNA-depleted mouse cell lines. Id. Thus, the cell functions more efficiently when there is compatibility between the DNA of the nucleus and mitochondrial genes of the cell.

Ordinarily, cells contain only one type of mitochondrial DNA. It has been published that following cytoplasmic transfer or transfer of a cell nucleus in animal cells, multiple different types of mitochondrial DNA or mismatching of mitochondrial DNA and DNA of the nucleus can result. See, for example, Spikings, et al. Hum. Rep. Update vol. 12, no. 4, pp. 401-415 (2006), which is incorporated herein by reference.

For example, mitochondrial cristae are the site of the electron transfer chain, the last stage in cellular respiration where oxidative phosphorylation takes place. Id. This aerobic process allows further metabolism of the products of anaerobic glycolysis and the citric acid cycle to produce carbon dioxide and water, with the subsequent release of 32 molecules of ATP. Id. The components of the electron transfer chain are encoded by both chromosomal and mitochondrial DNA (mtDNA), with all components being required for efficient function.

In an embodiment, the eukaryotic cell includes a cybrid formed by the genome of the nucleus from one source (e.g., endogenous) and the mitochondrial genome from another source (e.g., from a maternally genetically related cell). For example, Rho-zero cells (cells devoid of mitochondrial DNA) can be repopulated with exogenous mitochondrial DNA, resulting in transmitochondrial cybrids. Id. Alternatively, cells can be fused or chemically combined, resulting in cybrid or hybrid cells.

It has been published that genome of the nucleus and mitochondrial genomes interact and communicate in eukaryotic cells. See, for example, Poyton and McEwen, Ann. Rev. Biochem.; Abstract; vol. 65, pp. 563-607 (1996), which is incorporated herein by reference. For example, the genome of the nucleus encodes essential subunit polypeptides utilized in mitochondrial proteins, and is important for several reasons, including the regulation of oxidative energy production. Secondly, they collaborate in the synthesis and assembly of the proteins, which requires the bidirectional flow of information between the nucleus and the mitochondria. Id. In other published examples, the genome of the nucleus encodes proteins that account for about 90% of the protein mass of the mitochondria, including in all four mitochondrial compartments (inner and outer mitochondrial membranes, matrix, and intermembrane space). Id. By contrast, the mitochondrial genome specifies only a few proteins, which reside mainly in the inner mitochondrial membrane. Id. The mitochondrial genome also encodes RNA molecules that co-assemble with proteins encoded in the nucleus. Id.

It has been published that mitochondrial gene products are components of multimeric protein complexes that contain nucleus-encoded components as well. Id. For example, components common to all eukaryotic cells that utilize components encoded by both DNA of the nucleus, as well as mitochondrial DNA include coenzyme Q cytochrome c reductase, cytochrome c oxidase, $F_1F_0$ ATPase, and the mitochondrial ribosome. Id. In some eukaryotic cells, NADH dehydrogenase, small and large ribosomal subunits, RNase-P, and RNA splicing enzymes include chimeric components, as well. Id.

With regard to regulation of biosynthesis of mitochondrial proteins, trans-acting genes of the nucleus serve to modulate either the level of expression of mitochondrial genes or in the assembly of respiratory proteins. Id. In certain instances, trans-acting genes of the nucleus serve to modulate either the level of expression of the mitochondrial genome as a whole, or the expression of individual genes on the mitochondrial genome. Id. Furthermore, communication from the genome of the nucleus to the mitochondria involves proteins that are translated in the cytosol and imported into the mitochondria. Id. Communication from the mitochondria to the nucleus likely involves metabolic signals and one or more signal transduction pathways that function across the inner mitochondrial membrane. Id.

It has also been published that mitochondrial gene expression involves interactions between nucleus-coded gene products and the mitochondrial genome or its gene products at several junctions. For example, transcription of mitochondrial gene expression requires interaction with nucleus-coded gene products, RNA processing, and translation utilize various nucleus-coded gene products. Id.

In another example, the proteins encoded by nucleus genes are translated on cytosolic ribosomes (or ribosomes bound to the outer mitochondrial membrane), and are imported by the mitochondria posttranslationally, whereas proteins encoded by mitochondrial genes are translated on endogenous mitochondrial ribosomes that are bound to the matrix side of the inner membrane, and are inserted into it cotranslationally. Id.

It has been published that the genome of the nucleus exerts influence over mitochondrial gene expression as well as the import, export, and assembly pathways required for biogenesis of functional mitochondria. Id.

Thus, supplementation or complementation by mitochondrial replacement, mitochondrial DNA replacement, cell nucleus replacement, or nucleocytoplasmic replacement provides a basis for therapy for cells whose respiration ability is compromised (e.g., due to aging or disease). In certain instances, at least one of mitochondria, mitochondrial DNA, cell nucleus, or nucleocytoplasm is provided to a eukaryotic cell from a maternally genetically related cell. In some cases, the mitochondria, mitochondrial DNA, cell nucleus, or nucleocytoplasm is provided by way of a carrier (e.g., platelet, lipid, polymeric vehicle, etc.).

In an embodiment, a modified eukaryotic cell comprises at least one exogenous cellular component from a genetically maternally related source. In an embodiment, the at least one exogenous cellular component includes at least one of exogenous mitochondria, exogenous mitochondrial DNA, DNA of the cell nucleus, or exogenous cell nucleus. In an embodiment, the at least one exogenous cellular component is located in at least one intracellular compartment of the modified eukaryotic cell.

In an embodiment, a modified eukaryotic cell includes at least one exogenous cellular component from a genetically maternally related source.

In an embodiment, the intracellular compartment of a eukaryotic cell includes at least one of a nucleolus, nucleus, ribosome, vesicle, rough endoplasmic reticulum, Golgi apparatus, cytoskeleton, smooth endoplasmic reticulum, mitochondria, vacuole, cytoplasm, lysosome, or centriole. In an embodiment, the eukaryotic cell is located in at least one of in situ, in vitro, in vivo, in utero, in planta, in silico, or ex vivo.

In an embodiment, the eukaryotic cell is implantable or transplantable. In an embodiment, the eukaryotic cell is implanted or transplanted into at least one subject. In an embodiment, the eukaryotic cell is implanted or transplanted into at least one subject subsequent to modification. In an embodiment, the eukaryotic cell is implanted subsequent to modification, into the original subject from which it was extracted.

In an embodiment, at least one eukaryotic cell is selected for modification based on one or more eukaryotic cell parameters. In an embodiment, the one or more eukaryotic cell parameters relate to at least one property of the eukaryotic cell. In an embodiment, the one or more eukaryotic cell parameters include at least one of eukaryotic cell size, eukaryotic cell stage, eukaryotic cell quality, health of the subject from which the eukaryotic cell originates, species of the subject from which the eukaryotic cell originates, cleavage rate of the eukaryotic cell, metabolic profile of the eukaryotic cell, genomic profile of the eukaryotic cell, transcriptomic profile of the eukaryotic cell, proteomic profile of the eukaryotic cell, or storage conditions of the eukaryotic cell (if previously stored ex vivo). In an embodiment, the storage conditions of the eukaryotic cell include at least one of duration of storage time, storage temperature, storage size, eukaryotic cell dilution, or storage solution(s).

In an embodiment, a modified eukaryotic cell is produced by the process of providing at least one exogenous cellular component derived from a maternally genetically related eukaryotic cell. In an embodiment, the at least one exogenous cellular component includes at least one of exogenous mitochondria, exogenous mitochondrial DNA, or exogenous cell nucleus. In an embodiment, the eukaryotic cell is located in at least one of in situ, in vitro, in vivo, in utero, in planta, in silico, or ex vivo. In an embodiment, the eukaryotic cell is implantable or transplantable.

In an embodiment, the eukaryotic cell is implanted or transplanted into at least one subject. In an embodiment, the eukaryotic cell is implanted or transplanted into at least one subject subsequent to modification. In an embodiment, the at least one subject includes at least one of a plant, alga, or animal. In an embodiment, the at least one subject includes at least one of a vertebrate or invertebrate. In an embodiment, the at least one subject includes at least one of an amphibian, mammal, reptile, fish, or bird.

In an embodiment, the at least one subject includes at least one human. In an embodiment, the at least one subject includes at least one plant. In an embodiment, the at least one subject includes at least one of a food crop, ornamental, aquatic plant. In an embodiment, the modified eukaryotic cell further comprises one or more of a suspension, mixture, solution, sol, clathrate, colloid, emulsion, microemulsion, aerosol, ointment, capsule, micro-encapsule, powder, tablet, suppository, cream, device, paste, resin, liniment, lotion, ampule, elixir, spray, syrup, foam, pessary, tincture, detection material, polymer, biopolymer, buffer, adjuvant, diluent, lubricant, disintegration agent, suspending agent, solvent, light-emitting agent, colorimetric agent, glidant, anti-adherent, antistatic agent, surfactant, plasticizer, emulsifying agent, flavor, gum, sweetener, coating, binder, filler, compression aid, encapsulation aid, preservative, granulation agent, spheronization agent, stabilizer, adhesive, pigment, sorbent, nanoparticle, microparticle, prodrug, or gel.

In an embodiment, a modified eukaryotic cell comprises at least one exogenous cellular component from a genetically maternally related source. In an embodiment, the at least one exogenous cellular component includes at least one of exogenous mitochondria, exogenous mitochondrial DNA, DNA of the cell nucleus, or exogenous cell nucleus. In an embodiment, the at least one exogenous cellular component is located in at least one intracellular compartment of the modified eukaryotic cell. In an embodiment, the genetically maternally related source includes a genetically maternally related cell.

In an embodiment, a method includes modifying a eukaryotic cell by providing at least one exogenous cellular component obtained or derived from a maternally genetically related cell. In an embodiment, the exogenous cellular component includes at least one of exogenous mitochondria, exogenous mitochondrial DNA, DNA of the nucleus, or exogenous cell nucleus. In an embodiment, the exogenous mitochondrial DNA of the maternally genetically related cell includes fewer mutations than the endogenous mitochondrial DNA of the eukaryotic cell. In an embodiment, the endogenous mitochondrial DNA of the eukaryotic cell includes fewer mutations than the exogenous mitochondrial DNA of the maternally genetically related cell.

In an embodiment, the at least one of the exogenous mitochondria, exogenous mitochondrial DNA, or exogenous cell nucleus, is provided to at least one intracellular compartment of the eukaryotic cell. In an embodiment, the at least one exogenous cellular component is provided to the eukaryotic cell by way of at least one of endocytosis, injection or electroporation. In an embodiment, the intracellular compartment of the eukaryotic cell includes at least one of a nucleolus, cell nucleus, ribosome, vesicle, rough endoplasmic reticulum, Golgi apparatus, cytoskeleton, smooth endoplasmic reticulum, mitochondria, mitochondrial DNA, vacuole, cytoplasm, lysosome, cell wall, vacuole, plastid, chloroplast, leucoplast, chromoplast, ribosome, chromatin, or centriole.

In an embodiment, the method further comprises measuring the membrane potential of the eukaryotic cell or the maternally genetically related cell at least one of prior to, during, or subsequent to providing the at least one exogenous cellular component to the eukaryotic cell. In an embodiment, the at least one exogenous cellular component is extracted from the maternally genetically related cell. In an embodiment, the method further comprises measuring the membrane potential of at least one of the eukaryotic cell or the maternally genetically related cell at least one of prior to, during, or subsequent to providing the at least one exogenous cellular component to the eukaryotic ell.

In an embodiment, at least one exogenous cellular component is provided in response to the presence or level of at least one eukaryotic cell indicator. In an embodiment, the at least one eukaryotic cell indicator includes at least one indicator of one or more of a property of the eukaryotic cell; a property of administering the at least one mitochondria, mitochondrial DNA, or cell nucleus, to the eukaryotic cell; eukaryotic cell death; eukaryotic cell division; eukaryotic cell cytoskeletal rearrangement; eukaryotic cell mitochondrial quality, quantity, or arrangement; or eukaryotic cell or tissue secretion.

As described herein, in an embodiment, the property of the eukaryotic cell includes at least one of eukaryotic cell size, eukaryotic cell stage, eukaryotic cell quality, health of the subject from which the eukaryotic cell originates, species of the subject from which the eukaryotic cell originates, immunological background of the eukaryotic cell, mitotic rate of the eukaryotic cell, metabolic profile of the eukaryotic cell, genomic profile of the eukaryotic cell, transcriptomic profile of the eukaryotic cell, or proteomic profile of the eukaryotic cell, or storage conditions of the eukaryotic cell. In an embodiment, the storage conditions of the eukaryotic cell include at least one of duration of storage time, storage temperature, storage size, eukaryotic cell dilution, or storage solution(s).

In an embodiment, the at least one eukaryotic cell is selected for modifying based on one or more eukaryotic cell indicators. In an embodiment, the at least one maternally genetically related cell is selected for extraction of the at least one cellular component at least partially based on one or more eukaryotic cell indicators. In an embodiment, at least one of the eukaryotic cell or the maternally genetically related cell includes at least one of a blood cell, muscle cell, nerve cell, fibroblast, adipose cell, stem cell, pluripotent cell, epithelial cell, skin cell, liver cell, spleen cell, oocyte, Sertoli cell, neoplastic cell, hematopoietic stem cell, lymphocyte, thymocyte, neuronal stem cell, sperm cell, retinal cell, zygote, pancreatic cell, osteoclast, osteoblast, myocyte, embryonic stem cell, fetal cell, embryonic cell, keratinocyte, mucosal cell, mesenchymal stem cell, T cell, B cell, memory T cell, memory B cell, antigen presenting cell, lymphocyte, thymocyte, meristematic cell, parenchyma cell, collenchymas cell, sclerenchyma cell, or other cell.

In an embodiment, the method further comprises selecting the eukaryotic cell for further manipulation. In an embodiment, manipulation includes utilizing the selected eukaryotic cell for transplant or implant into a recipient subject. In an embodiment, manipulation includes at least one of cell membrane stripping, genetic modification, freezing, or fusing with another biological cell. In an embodiment, the maternally genetically related cell is derived from at least one of the mother, biological sibling, sister's child, or mother's sister's child of the source of the eukaryotic cell. In an embodiment, the maternally genetically related cell includes or is derived from at least one of an oocyte, or stem cell from at least one of the mother, biological sibling, sister's child, or mother's sister's child of the source of the eukaryotic cell. In an embodiment, the maternally genetically related cell is derived from the child of the source of the eukaryotic cell, wherein the source of the eukaryotic cell is female. In an embodiment, the maternally genetically related cell includes or is derived from at least one of an oocyte, or stem cell from the child of the source of the eukaryotic cell. In an embodiment, the source of the exogenous cellular component is of chronologically younger age than the source of the eukaryotic cell. In an embodiment, the source of the exogenous cellular component is of chronologically older age than the source of the eukaryotic cell.

In an embodiment, a method comprises administering a modified eukaryotic cell to a biological tissue; wherein the modified eukaryotic cell includes at least one exogenous cellular component derived from a genetically maternally related cell. In an embodiment, the at least one biological tissue is located in a subject. In an embodiment, the at least one eukaryotic cell is formulated for administration to at least one biological tissue by at least one route, including, among others, peroral, topical, transdermal, epidermal, intravenous, intraocular, tracheal, transmucosal, intracavity, subcutaneous, intramuscular, inhalation, fetal, intrauterine, intragastric, placental, intranasal, interdermal, intradermal, enteral, parenteral, surgical, or injection.

In an embodiment, the at least one exogenous cellular component includes at least one of exogenous mitochondria, exogenous mitochondrial DNA, DNA of a cell nucleus, or exogenous cell nucleus. In an embodiment, the exogenous mitochondrial DNA of the maternally genetically related cell includes fewer mutations than the endogenous mitochondrial DNA of the eukaryotic cell. In an embodiment, the endogenous mitochondrial DNA of the eukaryotic cell includes fewer mutations than the exogenous mitochondrial DNA of the maternally genetically related cell.

In an embodiment, a method, comprising: selecting at least one exogenous cellular component, at least partially based on one or more genetic characteristics of the endogenous mitochondrial DNA of a eukaryotic cell, and providing the at least one selected exogenous cell nucleus component to the eukaryotic cell. In an embodiment, the at least one exogenous cell nucleus component includes at least one of DNA of the cell nucleus, or an exogenous cell nucleus. In an embodiment, the method further comprises providing at least one of exogenous mitochondria, or exogenous mitochondrial DNA. In an embodiment, the mitochondrial DNA includes one or more mitochondrial chromosomes. In an embodiment, the at least one exogenous cell nucleus component is derived from a maternally genetically related cell. In an embodiment, selecting the at least one of exogenous cellular component is at least partially based on one or more alleles of one or more genes of at least one of the eukaryotic cell, or the maternally genetically related cell. In an embodiment, the method further comprises selecting the at least one exogenous cellular component at least partially based on the Major Histocompatibility genetic characteristics of at least one of the source of the eukaryotic cell or the source of the maternally genetically related cell.

In an embodiment, the method further comprises selecting the at least one exogenous cellular component at least partially based on one or more genetic characteristics of the DNA of the nucleus of at least one of the eukaryotic cell, or the maternally genetically related cell. In an embodiment, the method further comprises selecting the at least one exogenous cellular component at least partially based on the compatibility of the mitochondrial DNA of at least one of the eukaryotic cell, or the maternally genetically related cell. In an embodiment, the method further comprises selecting the at least one exogenous cellular component at least partially based on the compatibility of one or more alleles of the DNA of the nucleus of the maternally genetically related cell with the eukaryotic cell. In an embodiment, selecting the at least one exogenous cellular component includes searching at least one database including information related to genotyped mitochondrial DNA.

In an embodiment, the method further comprises selecting the at least one exogenous cellular component at least partially based on the chronological age of at least one of the source of the eukaryotic cell, or the source of the maternally genetically related cell. In an embodiment, the method further comprises selecting the at least one exogenous cellular component at least partially based on the number of mutations in the mitochondrial DNA of at least one of the eukaryotic cell, or the maternally genetically related cell.

In an embodiment, the at least one exogenous cellular component is provided to at least one intracellular compartment of the eukaryotic cell. As described herein, in an embodiment, the at least one intracellular compartment includes at least one of a nucleolus, nucleus, ribosome, vesicle, rough endoplasmic reticulum, Golgi apparatus, cytoskeleton, smooth endoplasmic reticulum, mitochondria, vacuole, cytoplasm, lysosome, or centriole. In an embodiment, at least one endogenous mitochondria, mitochondrial DNA, cell nucleus, or nucleocytoplasm, is at least partially removed from the eukaryotic cell prior to providing the at least one exogenous cellular component to the eukaryotic cell. In an embodiment, at least one of the endogenous mitochondria, mitochondrial DNA, cell nucleus, or nucleocytoplasm, is removed beyond detection from the eukaryotic cell prior to providing the at least one exogenous cellular component to the eukaryotic cell. In an embodiment, the method further comprises selecting the at least one exogenous cellular component at least partially based on the Major Histocompatibility type of at least one of the source of the eukaryotic cell or the maternally genetically related cell.

In an embodiment, the detection material includes at least one of a radioactive, luminescent, colorimetric fluorescent or odorous substance. In an embodiment, the at least one detection material includes at least one of a taggant, contrast agent, sensor, or electronic identification device. In an embodiment, the at least one electronic identification device includes at least one radio frequency identification device. In an embodiment, the at least one sensor receives information associated with at least one of temperature, pH, inflammation, presence of at least one substance, or biological response to administration of the composition. In an embodiment, the at least one detection material includes at least one of a diamagnetic particle, ferromagnetic particle, paramagnetic particle, super paramagnetic particle, particle with altered isotope, or other magnetic particle.

In an embodiment, one or more SNPs may alter one or more of a coding region, gene product, non-coding region, intergenic region, centromeric region, telomeric region, or RNA. In an embodiment, the one or more SNPs may be in linkage disequilibrium with one or more traits, alleles, or markers of chromosomal characteristics.

In an embodiment, one or more chromosomal characteristics include, among other things, one or more duplications, insertions, deletions, substitutions, replications, or breaks. In an embodiment, one or more chromosomal characteristics include haplotype or nucleic acid sequence. In an embodiment, one or more nucleic acid sequences include at least one of a repetitive sequence, telomeric sequence, centromeric sequence, mutated sequence, alternate sequence, intergenic sequence, protein coding sequence, or non-coding sequence. In an embodiment, the nucleic acid sequence is linked with one or more of a disease, disorder, syndrome, or condition, and optionally may encode a gene linked with one or more of a disease, disorder, syndrome, or condition.

In an embodiment, one or more genetic characteristics include one or more of a single nucleotide polymorphism, chromosomal characteristic, methylation pattern, or nucleic acid sequence. In an embodiment, one or more of these or other genetic characteristics are detected in at least one of the donor cell or recipient cell. In an embodiment, one or more of these genetic characteristics are utilized in analysis of at least one of the donor cell or recipient cell.

In an embodiment, at least one of the endogenous mitochondria, mitochondrial DNA, or cell nucleus is at least partially removed from the eukaryotic cell prior to providing at least one of the exogenous mitochondria, mitochondrial DNA, or cell nucleus. In an embodiment, the endogenous mitochondria, mitochondrial DNA, or cell nucleus is at least about 99%, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, at least about 10%, at least about 5%, at least about 1%, or any value less than or therebetween.

In an embodiment, a modified eukaryotic cell, produced by the process of providing at least one exogenous cellular component selected at least partially based on one or more genetic characteristics of the endogenous mitochondrial DNA. In an embodiment, the at least one exogenous cellular component includes at least one of exogenous mitochondria, exogenous mitochondrial DNA, or exogenous cell nucleus.

In an embodiment, a modified eukaryotic cell comprises at least one exogenous cellular component compatible with the genetic characteristics of the endogenous mitochondrial DNA of the eukaryotic cell.

Kits

In an embodiment, kits are included for any of the various aspects disclosed herein. For example, in an embodiment, a kit includes a detection material responsive to at least one eukaryotic cell indicator, and means for administering at least one exogenous energy supplying factor to at least one eukaryotic cell. In an embodiment, the kit includes the at least one exogenous energy supplying factor (e.g., pyruvate, ATP, glucose or other carbohydrate, etc.). In an embodiment, the kit includes a delivery device. In an embodiment, the kit includes at least one tool for selecting at least one eukaryotic cell for manipulation. In an embodiment, a kit includes standard packaging or instructions for use.

In an embodiment, a kit comprises: a detection material responsive to at least one eukaryotic cell indicator, and means for providing at least one exogenous cellular component to at least one eukaryotic cell. In an embodiment, the detection material includes at least one of a radioactive, luminescent, colorimetric fluorescent or odorous substance. In an embodiment, the at least one detection material includes at least one of a taggant, contrast agent, magnetic particle, particle with altered isotope, or electronic identification device. In an embodiment, the at least one electronic identification device includes at least one radio frequency identification device. In an embodiment, the at least one magnetic particle includes at least one paramagnetic particle, ferromagnetic particle, super paramagnetic particle, diamagnetic particle, or other magnetic particle. In an embodiment, the kit further comprises at least one sensor. In an embodiment, the at least one sensor is configured to receive information associated with at least one of temperature, pH, inflammation, presence of at least one substance, detection material, or biological response to administration of at least one of the exogenous mitochondria, mitochondrial DNA, cell nucleus, or nucleocytoplasm. In an embodiment, the at least one sensor is configured to receive information associated with at least one eukaryotic cell indicator. In an embodiment, the at least one detection material includes at least one of a diamagnetic particle, ferromagnetic particle, paramagnetic particle, super paramagnetic particle, particle with altered isotope, or other magnetic particle.

In an embodiment, a kit comprises: a detection material responsive to at least one eukaryotic cell indicator, and means for providing at least one exogenous cellular component to at least one eukaryotic cell, wherein the exogenous cellular component is selected based at least in part on one or more genetic characteristics of the endogenous mitochondrial DNA. In an embodiment, the detection material includes at least one of a radioactive, luminescent, colorimetric fluorescent or odorous substance. In an embodiment, the at least one detection material includes at least one of a taggant, contrast agent, magnetic particle, particle with altered isotope, or electronic identification device. In an embodiment, the at least one electronic identification device includes at least one radio frequency identification device.

In an embodiment, the at least one magnetic particle includes at least one paramagnetic particle, ferromagnetic particle, super paramagnetic particle, diamagnetic particle, or other magnetic particle. In an embodiment, the kit further comprises at least one sensor. In an embodiment, the at least one sensor is configured to receive information associated with at least one of temperature, pH, inflammation, presence of at least one substance, detection material, or biological response to administration of at least one of the exogenous mitochondria, mitochondrial DNA, cell nucleus, or nucleocytoplasm. In an embodiment, the at least one sensor is configured to receive information associated with at least one eukaryotic cell indicator. In an embodiment, the at least one detection material includes at least one of a diamagnetic particle, ferromagnetic particle, paramagnetic particle, super paramagnetic particle, particle with altered isotope, or other magnetic particle.

As indicated in the Figures, FIG. 1 illustrates a cell 100, including a cell membrane 130, a nucleus 120 with a membrane of the nucleus 140, cytoplasm 160, endoplasmic reticulum 170, Golgi bodies 180, mitochondria 150. In an embodiment, at least one mitochondrion of the donor cell is transplanted to the recipient cell. In an embodiment, the donor and recipient cells are maternally genetically related.

Figure 2:
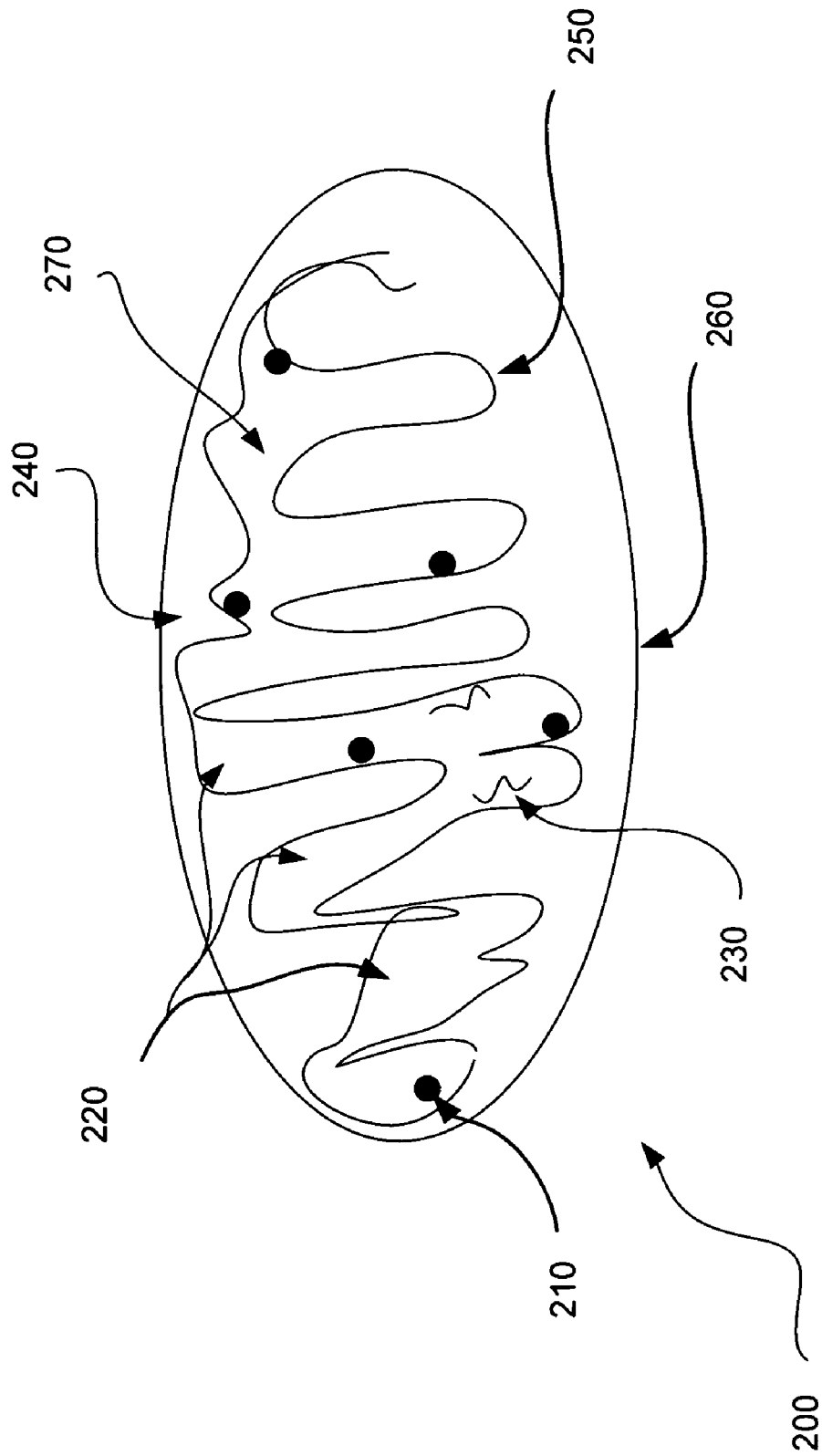
FIG. 2 illustrates a partial view of an example of a mitochondrion, including various components.

FIG. 2 illustrates a transverse view of an example of a mitochondrion 200, including cristae 220, mitochondrial DNA 230, granules 210, an outer mitochondrial membrane 260, an inter membrane space 240, an inner matrix 270, and an inner mitochondrial membrane 250.

Figure 3:
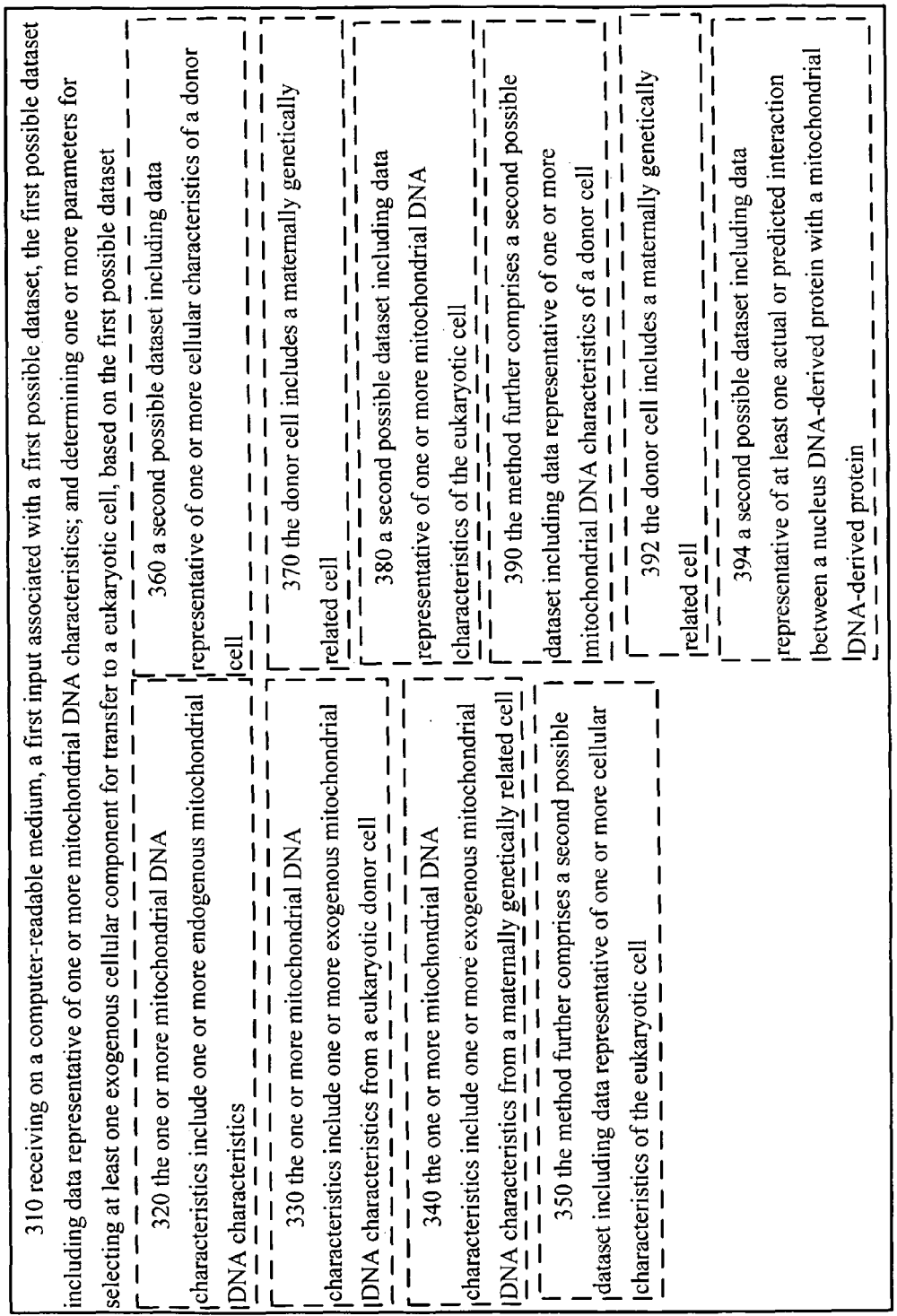
FIG. 3 illustrates a partial view of a particular embodiment of a method.

FIG. 3 illustrates a method, comprising 310 receiving on a computer-readable medium, a first input associated with a first possible dataset, the first possible dataset including data representative of one or more mitochondrial DNA characteristics; and determining one or more parameters for selecting at least one exogenous cellular component for transfer to a eukaryotic cell, based on the first possible dataset. In an embodiment 320, the one or more mitochondrial DNA characteristics include one or more endogenous mitochondrial DNA characteristics. In an embodiment 330, the one or more mitochondrial DNA characteristics include one or more exogenous mitochondrial DNA characteristics from a eukaryotic donor cell. In an embodiment 340, the one or more mitochondrial DNA characteristics include one or more exogenous mitochondrial DNA characteristics from a maternally genetically related cell. In an embodiment, 350 the method further comprises a second possible dataset including data representative of one or more cellular characteristics of the eukaryotic cell. In an embodiment, 360 the method further comprises a second possible dataset including data representative of one or more cellular characteristics of a donor cell. In an embodiment 370, the donor cell includes a maternally genetically related cell. In an embodiment 380, the method further comprises a second possible dataset including data representative of one or more mitochondrial DNA characteristics of the eukaryotic cell. In an embodiment 390, the method further comprises a second possible dataset including data representative of one or more mitochondrial DNA characteristics of a donor cell. In an embodiment 392, the donor cell includes a maternally genetically related cell. In an embodiment 394, the method further comprises a second possible dataset including data representative of at least one actual or predicted interaction between a nucleus DNA-derived protein with a mitochondrial DNA-derived protein.

As illustrated in FIG. 4, in an embodiment 400, the at least one exogenous cellular component includes at least one of exogenous mitochondria, exogenous mitochondrial DNA, exogenous cell nucleus, exogenous DNA from the nucleus, or exogenous nucleocytoplasm. In an embodiment 410, wherein receiving on a computer-readable medium a first input associated with a first possible dataset, comprises: receiving the first input associated with the first possible dataset, the first input including data representative of one or more of the one or more mitochondrial DNA characteristics. In an embodiment 420, wherein receiving on a computer-readable medium a first input associated with a first possible dataset, comprises: receiving the first input associated with the first possible dataset, the first input including data representative of one or more of the one or more mitochondrial DNA characteristics, including at least one of a genetic attribute, single nucleotide polymorphism, haplotype, allelic marker, allele, disease marker, genetic abnormality, genetic disease, genetic mutation, inversion, deletion, duplication, recombination, nucleic acid sequence, gene, protein coding sequence, intron, exon, regulatory sequence, intergenic sequence, mitochondrial nucleic acid sequence, mitochondria, methylation pattern, or epigenetic element.

In an embodiment 430, wherein receiving on a computer-readable medium a first input associated with a first possible dataset comprises: receiving the first input associated with the first possible dataset, the first input including data representative of one or more mitochondrial DNA characteristics of at least one of a genome, or nucleic acid. In an embodiment 440, receiving on a computer-readable medium a first input associated with a first possible dataset comprises: receiving a first data entry associated with the first possible dataset. In an embodiment 450, receiving on a computer-readable medium a first input associated with a first possible dataset comprises: receiving a first data entry associated with the first possible dataset, the first data entry including data representative of one or more of the one or more mitochondrial DNA characteristics. In an embodiment 460, wherein receiving on a computer-readable medium a first data entry associated with a first possible dataset, the first data entry including data representative of one or more of the at least one mitochondrial DNA characteristics, comprises: receiving on a computer-readable medium a first data entry associated with the first possible dataset, the first data entry including data representative of one or more of the one or more mitochondrial DNA characteristics, including at least one of a genetic attribute, single nucleotide polymorphism, haplotype, allelic marker, allele, disease marker, genetic abnormality, genetic disease, chromosomal abnormality, genetic mutation, inversion, deletion, duplication, recombination, chromosome, nucleic acid sequence, gene, protein coding sequence, intron, exon, regulatory sequence, intergenic sequence, mitochondrial nucleic acid sequence, mitochondria, telomere, telomere repeat, telomere length, centromere repeat, centromere, methylation pattern, or epigenetic element.

As illustrated in FIG. 5, in an embodiment 500, receiving on a computer-readable medium a first input associated with a first possible dataset comprises: receiving on a computer-readable medium a first data entry from a graphical user interface. In an embodiment 510, receiving on a computer-readable medium a first input associated with a first possible dataset comprises: receiving on a computer-readable medium a first data entry from at least one submission element of a graphical user interface. In an embodiment 520, receiving on a computer-readable medium a first input associated with a first possible dataset comprises: receiving on a computer-readable medium a first data entry at least partially identifying one or more elements of the first possible dataset. In an embodiment 530, receiving on a computer-readable medium a first data entry at least partially identifying one or more elements of the first possible dataset comprises: receiving on a computer-readable medium the first data entry at least partially identifying the one or more elements of the first possible dataset, one or more of the one or more elements including data representative of one or more genetic characteristics. In an embodiment 540, receiving on a computer-readable medium a first data entry at least partially identifying the one or more elements of the first possible dataset comprises: receiving on a computer-readable medium the first data entry at least partially identifying one or more elements of the first possible dataset, one or more of the one or more elements including data representative of one or more of the at least one of a genome, chromosome, or nucleic acid. In an embodiment 550, receiving on a computer-readable medium a first data entry at least partially identifying one or more elements of the first possible dataset comprises: receiving on a computer-readable medium the first data entry at least partially identifying the one or more elements of the first possible dataset, one or more of the one or more elements including data representative of at least one biological tissue or biological cell. In an embodiment 560, the at least one biological cell includes one of a blood cell, muscle cell, nerve cell, fibroblast, adipose cell, stem cell, pluripotent cell, epithelial cell, skin cell, liver cell, spleen cell, oocyte, Sertoli cell, neoplastic cell, hematopoietic stem cell, lymphocyte, thymocyte, neuronal stem cell, sperm cell, retinal cell, pancreatic cell, osteoclast, osteoblast, myocyte, embryonic stem cell, fetal cell, embryonic cell, keratinocyte, mucosal cell, mesenchymal stem cell, T cell, B cell, memory T cell, memory B cell, antigen presenting cell, lymphocyte, thymocyte, meristematic cell, parenchyma cell, collenchymas cell, sclerenchyma cell, or other cell.

As illustrated in FIG. 6, in an embodiment 600, the method further comprises accessing the first possible dataset in response to the first input. In an embodiment 610, accessing the first possible dataset in response to the first input comprises: accessing the first possible dataset in response to the first input, the first input including data representative of one or more of the at least one mitochondrial genetic characteristic. In an embodiment 620, accessing the first possible dataset in response to the first input comprises: accessing the first possible dataset from within a first database associated with a plurality of genetic characteristics. In an embodiment 630, accessing the first possible dataset in response to the first input comprises: accessing the first possible dataset by associating one or more of the at least one mitochondrial genetic characteristic with one or more elements of the first possible dataset.

In an embodiment 640, accessing the first possible dataset in response to the first input comprises: accessing the first possible dataset using a database management system engine configured to query a first database to retrieve the first possible dataset therefrom. In an embodiment 650, accessing the first possible dataset in response to the first input comprises: accessing the first possible dataset by corresponding one or more of the at least one mitochondrial genetic characteristic with one or more elements of the first possible dataset. In an embodiment 660, accessing the first possible dataset by corresponding one or more of the one or more mitochondrial DNA characteristics with one or more elements of the first possible dataset comprises: accessing the first possible dataset by corresponding one or more of the one or more mitochondrial DNA characteristics including at least one of a genetic attribute, single nucleotide polymorphism, haplotype, allelic marker, allele, disease marker, genetic abnormality, genetic disease, chromosomal abnormality, genetic mutation, inversion, deletion, duplication, recombination, chromosome, nucleic acid sequence, gene, protein coding sequence, intron, exon, regulatory sequence, intergenic sequence, mitochondrial nucleic acid sequence, mitochondria, telomere, telomere repeat, telomere length, centromere repeat, centromere, methylation pattern, or epigenetic element with the one or more elements of the first possible dataset.

As illustrated in FIG. 7, in an embodiment 700, accessing the first possible dataset in response to the first input comprises: accessing the first possible dataset as being associated with one or more of the one or more mitochondrial DNA characteristics, based on one or more characterizations stored in association with one or more elements of the first possible dataset. In an embodiment 710, accessing the first possible dataset in response to the first input comprises: accessing the first possible dataset as being associated with one or more of the one or more mitochondrial DNA characteristics, based on one or more characterizations stored in association with one or more elements of the first possible dataset, the one or more elements including one or more genetic characteristics. In an embodiment 720, receiving on a computer-readable medium a first input associated with a first possible dataset comprises: receiving on a computer-readable medium a first request associated with the first possible dataset. In an embodiment 730, receiving on a computer-readable medium a first input associated with a first possible dataset comprises: receiving on a computer-readable medium a first request associated with the first possible dataset, the first request selecting one or more of the one or more mitochondrial DNA characteristics.

In an embodiment 740, receiving a first input associated with a first possible dataset comprises: receiving on a computer-readable medium a first request from a graphical user interface. In an embodiment 750, receiving on a computer-readable medium a first input associated with a first possible dataset comprises: receiving on a computer-readable medium a first request from at least one submission element of a graphical user interface. In an embodiment 760, receiving on a computer-readable medium a first input associated with a first possible dataset comprises: receiving on a computer readable medium a first request, the first request at least partially identifying one or more elements of the first possible dataset. In an embodiment 770, receiving on a computer-readable medium a first input associated with a first possible dataset comprises: receiving on a computer-readable medium a first request, the first request selecting one or more elements of the first possible dataset. In an embodiment 780, receiving on a computer-readable medium a first input associated with a first possible dataset comprises: receiving on a computer-readable medium a first request, the first request providing instructions at least partially identifying one or more of the one or more mitochondrial DNA characteristics.

As illustrated in FIG. 8, in an embodiment 800, receiving on a computer-readable medium a first input associated with a first possible dataset comprises: receiving on a computer-readable medium a first request, the first request providing instructions for determining one or more of the one or more mitochondrial DNA characteristics. In an embodiment 810, receiving on a computer-readable medium a first input associated with a first possible dataset comprises: accessing the first possible dataset in response to a first request, the first request specifying one or more of the one or more mitochondrial DNA characteristics and at least one other instruction. In an embodiment 820, the method further comprises: generating with a computer-recordable medium, the first possible dataset in response to the first input. In an embodiment 830, generating with a computer-recordable medium, the first possible dataset in response to the first input comprises: generating with a computer-recordable medium, the first possible dataset in response to the first input, the first input including data representative of one or more of the one or more mitochondrial DNA characteristics. In an embodiment 840, generating with a computer-recordable medium the first possible dataset in response to the first input comprises: generating with a computer-recordable medium, the first possible dataset from within a first database associated with a plurality of genetic characteristics.

In an embodiment 850, generating with a computer-recordable medium, the first possible dataset in response to the first input comprises: generating with a computer-recordable medium, the first possible dataset by associating one or more of the one or more mitochondrial DNA characteristics with one or more elements of the first possible dataset. In an embodiment 860, generating with a computer-recordable medium, the first possible dataset in response to the first input comprises: generating with a computer-recordable medium the first possible dataset using a database management system engine configured to query a first database to retrieve the first possible dataset therefrom.

As illustrated in FIG. 9, in an embodiment 900, generating with a computer-recordable medium, the first possible dataset in response to the first input comprises: generating with a computer-recordable medium, the first possible dataset by corresponding one or more of the one or more mitochondrial DNA characteristics with one or more elements of the first possible dataset. In an embodiment 910, receiving on a computer-readable medium a first input associated with a first possible dataset comprises: receiving on a computer-readable medium a first request associated with the first possible dataset. In an embodiment 920, receiving on a computer-readable medium the first input associated with a first possible dataset comprises: receiving on a computer-readable medium a first request associated with the first possible dataset, the first request selecting one or more of the one or more mitochondrial DNA characteristics. In an embodiment 930, receiving on a computer-readable medium a first input associated with a first possible dataset comprises: receiving on a computer-readable medium a first request from a graphical user interface. In an embodiment 930, receiving on a computer-readable medium a first input associated with a first possible dataset comprises: receiving on a computer-readable medium a first request from at least one submission element of a graphical user interface. In an embodiment 940, receiving on a computer-readable medium a first input associated with a first possible dataset comprises: receiving on a computer-readable medium a first request, the first request at least partially identifying one or more elements of the first possible dataset. In an embodiment 950, receiving on a computer-readable medium a first input associated with a first possible dataset comprises: receiving on a computer-readable medium a first request, the first request selecting one or more elements of the first possible dataset. In an embodiment 960, receiving on a computer-readable medium a first input associated with a first possible dataset comprises: receiving on a computer-readable medium a first request, the first request providing instructions at least partially identifying one or more of the one or more mitochondrial DNA characteristics. In an embodiment 970, receiving on a computer-readable medium a first input associated with a first possible dataset comprises: receiving on a computer-readable medium a first request, the first request providing instructions for determining one or more of the one or more mitochondrial characteristics.

As illustrated in FIG. 10, in an embodiment 1000, receiving on a computer-readable medium a first input associated with a first possible dataset comprises: receiving on a computer-readable medium a first request associated with the first possible dataset; and generating with a computer-recordable medium the first possible dataset in response to the first request, the first request specifying one or more of the one or more mitochondrial DNA characteristics and at least one other instruction. In an embodiment 1010, receiving on a computer-readable medium a first input associated with a first possible dataset comprises: receiving on a computer-readable medium a first request, the first request specifying one or more of the one or more mitochondrial DNA characteristics; and generating with a computer-recordable medium the first possible dataset in response to the first request at least partially by performing an analysis of one or more of the one or more mitochondrial DNA characteristics. In an embodiment 1020, the method further comprises determining a graphical illustration of the first possible dataset. In an embodiment 1030, determining a graphical illustration of the first possible dataset comprises: determining the graphical illustration for inclusion in a display element of a graphical user interface. In an embodiment 1040, determining a graphical illustration of the first possible dataset comprises: performing an analysis of one or more elements of the first possible dataset to determine a first possible outcome; and determining the graphical illustration based at least in part on the analysis. In an embodiment 1050, determining a graphical illustration of the first possible dataset comprises:

performing an analysis of one or more elements of the first possible dataset to determine a first possible outcome, the first possible outcome including one or more of a possible risk, a possible result, a possible consequence, a likelihood of success, or a cost; and determining the graphical illustration based on the analysis. In an embodiment 1060, determining a graphical illustration of the possible dataset comprises: performing an analysis of one or more elements of the first possible dataset to determine a first possible outcome, the first possible outcome including one or more of a predicted risk, predicted result, predicted consequence; and determining the graphical illustration based on the analysis. In an embodiment 1070, determining the graphical illustration of the first possible dataset comprises: performing an analysis of one or more elements of the first possible dataset to determine a first possible outcome, the first possible outcome including one or more of a predicted risk, predicted result, or predicted consequence; and determining the graphical illustration including one or more of the one or more mitochondrial characteristics in association with a visual indicator related to the first possible outcome.

As illustrated in FIG. 11, in an embodiment 1100, determining a graphical illustration of the first possible dataset comprises: determining a correlation between a first possible outcome and a type or characteristic of a visual indicator used in the graphical illustration to represent the first possible outcome. In an embodiment 1110, the at least one exogenous cellular component is derived from a maternally genetically related cell.

As illustrated in FIG. 12, in an embodiment, a computer program product, comprises 1210 a computer-recordable medium bearing at least one of one or more instructions for receiving a first input associated with a first possible dataset, the first possible dataset including data representative of one or more mitochondrial DNA characteristics; wherein at least one of the one or more mitochondrial DNA characteristics is a genetic characteristic; and one or more instructions for determining parameters for selecting one or more characteristics based on one or more of a mitochondria, mitochondrial DNA, cell nucleus, or nucleocytoplasm, from the first possible dataset. In an embodiment 1220, the computer program product further comprises one or more instructions for accessing the first possible dataset in response to the first input. In an embodiment 1230, the computer program product further comprises one or more instructions for generating the first possible dataset in response to the first input. In an embodiment 1240, the computer program product further comprises: one or more instructions for determining a graphical illustration of the first possible dataset. In an embodiment 1250, the computer-recordable medium includes a computer-readable medium. In an embodiment 1260, the computer-recordable medium includes a recordable medium. In an embodiment 1270, the computer-recordable medium includes a communications medium.

As illustrated in FIG. 13, in an embodiment 1300, a system comprises 1310 a computing device; and instructions that when executed on the computing device cause the computing device to receive a first input associated with a first possible dataset, the first possible dataset including data representative of one or more mitochondrial DNA characteristics; wherein at least one of the one or more mitochondrial DNA characteristics is a genetic characteristic; and instructions that when executed on the computing device cause the computing device to determine parameters for selecting at least one exogenous cellular component for transfer to a eukaryotic cell based on the first possible dataset. In an embodiment 1320, the at least one exogenous cellular component includes at least one of exogenous mitochondria, exogenous mitochondrial DNA, exogenous cell nucleus, or exogenous nucleocytoplasm. In an embodiment 1330, the at least one exogenous cellular component is derived from a maternally genetically related cell. In an embodiment 1340, the system further comprises: instructions that when executed on the computing device cause the computing device to access the first possible dataset in response to the first input. In an embodiment 1350, the system further comprises: instructions that when executed on the computing device cause the computing device to generate the first possible dataset in response to the first input. In an embodiment, the system further comprises: instructions that when executed on the computing device cause the computing device to determine a graphical illustration of the first possible dataset. In an embodiment 1360, the computing device comprises: one or more of a desktop computer, workstation computer, computing system, cluster of processors, networked computer, tablet personal computer, laptop computer, or personal digital assistant. In an embodiment 1370, the computing device is operable to communicate with a database to access the first possible dataset. In an embodiment 1380, the computing device is operable to communicate with an apparatus configured to select the at least one exogenous cellular component for transfer into the eukaryotic cell.

The following Examples are intended to be illustrative of particular embodiments, and are not intended to be limiting in any way.

PROPHETIC EXAMPLES

Example 1

Modification of Mesenchymal Stem Cells with Maternally Genetically Related Mitochondria A method is described for modifying mesenchymal stem cells with mitochondria from maternally genetically related donor cells prior to autologous transplantation of the stem cells into a subject with amyotrophic lateral sclerosis (ALS). Autologous mesenchymal stem cell transplantation into the spinal cord is being used as a treatment option to attenuate neurodegeneration in individuals with ALS (Mazzini, et al. *Exp. Neurology*; Abstract; 223:229-237 (2010), which is incorporated herein by reference). Impaired mitochondrial function is a potential causal factor in neuronal dysfunction and degeneration in adult neurodegenerative diseases and is exemplified by reduced mitochondrial gene copy numbers and increased mitochondrial DNA gene deletions in surviving spinal neurons of individuals with ALS (Keeney & Bennett, *Mol. Neurodegener.* 5:21 (2010), which is incorporated herein by reference). Modifying mesenchymal stem cells with mitochondria from healthy maternally genetically related cells prior to autologous transplantation provides a means for improving mitochondrial function.

Platelets are used as a minimally invasive source of donor mitochondria. In addition, platelets lack DNA of the nucleus and are capable of transferring mitochondria to target cells through cellular fusion (Bacman & Moraes *Methods Cell Biol.* 80:503-524 (2007), which is incorporated herein by reference). Blood is drawn from a maternally genetically related subject into sterile acid citrate dextrose anticoagulant and centrifuged twice at 200×g for 15 min to pellet red and white blood cells; the resultant platelet-rich plasma is used as the source of platelets. Platelets are isolated by centrifugation of the platelet-rich plasma at 1,400×g for 10 min, and washed twice in washing solution 1 (12.72 mM sodium citrate, 2.99 mM glucose, 9.41 mM NaCl, 0.55 mM EDTA), and washed once in washing solution 2 (1 mM Tris-HCl, 2.99 mM glucose, 15.38 mM NaCl, 0.55 mM EDTA, pH 7.4).

Mitochondria are isolated from the platelets by cell lysis, followed by differential centrifugation (Silvagno, et al. *PLoS ONE* 5(1):e8670 (2010), which is incorporated herein by reference). Briefly, the platelets are resuspended in a hypotonic lysis buffer (10 mM Tris-HCl, pH 7.4 and 1% protease inhibitor solution) and incubated on ice for 30 minutes. The platelets are lysed by five passages through an insulin syringe needle to generate a total cell extract. The total cell extract is layered on a linear 30-50% sucrose gradient and centrifuged at 134,000×g for 120 minutes in a Beckman SW40 Ti rotor. The resulting particulate bands are diluted in 0.29 M sucrose and pelleted by centrifugation at 100,000×g for 60 minutes.

Alternatively, mitochondria are isolated from lysed platelets using a commercially available mitochondria isolation kit (e.g. Mitochondria Isolation Kit for Cultured Cells, Mito-Sciences, Eugene, Oreg.). The donor mitochondria isolated from the maternally genetically related cells are analyzed for presence or absence of specific mitochondrial properties prior to insertion of the donor mitochondria into mesenchymal stem cells. Mitochondrial DNA in intact mitochondria can be screened for mutations using specific peptide nucleic acid (PNA) oligomers conjugated to a membrane permeable reagent such as, for example, triphenylphosphonium (see, e.g., Muratovska, et al. *Nucleic Acids Res.* 29:1852-1863 (2001), which is incorporated herein by reference). A PNA oligomer is designed with a DNA sequence complimentary to a specific mitochondrial sequence, either normal or mutated, and used to assess whether a specific mitochondria contains DNA with that specific sequence.

For this analysis, PNA oligomers are conjugated to triphenylphosphonium by pretreating the PNA with 10 mM HEPES, 1 mM EDTA, and 250 nM 2-mercaptoethanol for 1 hour at 40° C. followed by incubation with iodobutyltriphenylphosphonium in HEPES/EDTA/ethanol for an additional 4 hours. The conjugated PNA is purified using reverse phase HPLC. The PNA is further conjugated to a fluorescent dye, such as FITC, TRITC, and/or BODIPY® derivatives, and/or quantum dots (see, e.g., Dahan *Histochem. Cell Biol.*; Abstract; 125:451-456 (2006), which is incorporated herein by reference). Relative binding of the fluorescent PNA to the complementary site within the mitochondrial DNA is assessed using either fluorescence microscopy, or fluorescence activated cell sorting. Additional PNA probes are used as negative and positive controls of DNA binding to ensure that the assay system is working. The analysis of donor mitochondria can be compared with that of the recipient mitochondria and/or published information regarding mitochondrial DNA to ensure that the donor mitochondria are healthy.

Autologous mesenchymal stem cells are isolated from the bone marrow of the ALS patient. Bone marrow is collected by aseptic aspiration from the posterior iliac crest using standard procedures. Ex vivo expansion of mesenchymal stem cells is carried out essentially as described by Pittenger, et al. *Science*, Abstract; 284:143-147 (1999), which is incorporated herein by reference). Briefly, the bone marrow is diluted in four volumes of Minimum Essential Medium Alpha Medium containing 10% fetal bovine serum and centrifuged at 900×g for 15 minutes. The cells are washed in phosphate-buffered saline and plated into an expansion medium containing Dulbecco's Minimum Essential Medium supplemented with 40% MCDB-201, 10% fetal bovine serum, insulin-transferrin-sodium selenite supplement, linoleic acid-bovine serum albumin, $10^{-8}$ M dexamethasone, $10^{-4}$ M ascorbic acid 2-phosphate, 50 U/ml penicillin/streptomycin, 10 ng/ml human platelet-derived growth factor-BB, and 10 ng/ml human epithelial growth factor. The cells are expanded over several passages prior to transplantation.

Donor mitochondria isolated from the maternally genetically related cells are inserted into cells with existing endogenous mitochondrial DNA, creating a heteroplasmic state. Alternatively, donor mitochondria are inserted into cells lacking endogenous mitochondrial DNA. Cells lacking mitochondrial DNA, termed $\rho^0$ cells, are generated by sustained treatment of cells with a toxin, e.g., ethidium bromide, at a concentration that blocks mitochondrial DNA replication with only minimal effect on DNA of the nucleus (see, e.g., U.S. Pat. No. 5,888,498; Yoon & Koob, *Nucleic Acids Res.* 31:1407-1415 (2003), which are incorporated herein by reference). Briefly, the mesenchymal stem cells isolated from a patient with ALS are exposed to 5 µg/ml ethidium bromide for 4 weeks in high-glucose medium supplemented with 50 µg/ml uridine and 0.1 mg/ml sodium pyruvate. At the end of 4 weeks, clonal $\rho^0$ cells are isolated by clonal dilution of the ethidium bromide treated cells. PCR with mitochondrial DNA specific primers as well as enzyme assays for cyanide-inhibitable oxygen utilization and complex I or cytochrome c oxidase activity are used to verify the $\rho^0$ state of a clonal population. $\rho^0$ cells can also be generated using other mitochondrial toxins including ditercalinium, rhodamine 6G, dideoxycytidine, streptozotocin (Inoue et al. *J. Biol. Chem.* 272:15510-15515 (1997); Bacman & Moraes, *Methods Cell Biol.* 80:503-524 (2007), which are incorporated herein by reference).

The donor mitochondria from the maternally genetically related cells are transferred into the mesenchymal stem cells using cellular fusion in which a cell containing mitochondrial DNA, e.g., a donor platelet, is fused with a cell lacking mitochondrial DNA, e.g., $\rho^0$ mesenchymal stem cells (see, e.g. Bacman & Moraes, *Methods Cell Biol.* 80:503-524 (2007); Kagawa & Hayashi *Gene Ther.* 4:6-10 (1997); Pye et al. *Nucleic Acids Res.* 34:e95 (2006) which are incorporated herein by reference). Fusion is carried out by incubating the two cell populations in the presence of polyethylene glycol (PEG). The $\rho^0$ mesenchymal stem cells are combined with the donor platelets for several hours in growth medium, allowing cell-cell contacts to be made. The medium is completely removed, and PEG 1450 is added to the cells for a brief 30 to 60 second period at which time the PEG is removed and the cells washed. The cells are cultured under selection conditions such that only the fused cells survive.

The modified mesenchymal stem cells are suspended in 1-2 ml of autologous cerebrospinal fluid and injected at multiple sites using a micrometric pump injector into the anterior horns of spinal cord of the ALS patient.

Example 2

Modification of Myoblast Cells with Maternally Genetically Related Mitochondrial DNA A method is described for modifying myoblast cells with mitochondria from maternally genetically related donor cells prior to autologous transplantation of the myoblast cells into a subject with heart failure. Autologous myoblast cell transplantation into cardiac tissue has been tested as a treatment option for individuals with congestive heart failure and myocardial infarction, as a means for replacing irreversibly damaged cardiomyocytes (see, e.g., Opie and Dib, *Nat. Clin. Pract. Cardiovasc. Med.* 3 Suppl 1:S42-5 (2006), which is incorporated herein by reference). Impaired mitochondrial function associated with aging is a potential causal factor in the decline in cardiac muscle function (see, e.g., Marin-Garcia, et al. *Cardiovasc. Drugs Ther.*; Abstract; 20:477-491 (2006), which is incorporated herein by reference). Modifying myoblast cells with mitochondria from healthy maternally genetically related cells prior to autologous transplantation provides a means for improving mitochondrial function.

Lymphocytes are used as a minimally invasive source of donor mitochondria (Choo-Kang et al. *Diabetes* 51:2317-2320 (2002), which is incorporated herein by reference). Blood is drawn from a maternally genetically related subject using standard procedures. Ideally the donor is younger than the intended recipient. Lymphocytes are isolated from the blood by centrifugation through Ficoll-Hypaque Plus (Amersham Biosciences, Piscataway, N.J.) and incubated for 3 hours at 37° C. in RPMI 1640 medium supplemented with 10% fetal bovine serum (FBS), 50 units/ml penicillin and 50 mg/ml streptomycin. After 3 hours, the non-adherent lymphocytes are removed and further cultured in fresh medium for an additional 48 hours.

Mitochondria are isolated from the lymphocytes by cell lysis, followed by differential centrifugation (Carpentieri & Sordahl, *Cancer Res.* 40:221-224 (1980), which is incorporated herein by reference). Briefly, the lymphocytes are lysed in 0.25 M sucrose, 5 mM Tri-HCl, 5 mM EGTA, and 0.5% bovine serum albumin using a tight fitting Teflon® pestle attached to a motor rotating at approximately 6000 rpm, a tissue homogenizer (e.g. Tekmar Tissumizer, Tekmar Co. Cincinnati Ohio), or a Dounce homogenizer. The homogenate is centrifuged at 480×g for 10 minutes to remove nuclei and heavier cellular debris. The supernatant is then centrifuged at 10,000×g for 10 minutes to generate a mitochondrial pellet. Alternatively, mitochondria are isolated from lymphocytes using a commercially available mitochondria isolation kit (e.g. Mitochondria Isolation Kit for Cultured Cells, Mito-Sciences, Eugene, Oreg.).

To isolate mitochondrial DNA, the isolated mitochondria derived from the lymphocytes of a maternally genetically related donor are incubated in 4000 Kunitz units of DNase I at 37° C. for 1 hour to eliminate any residual DNA of the nucleus. The treated mitochondria are subsequently washed through a series of sucrose gradients to remove the DNase I activity. Following DNase I treatment, the mitochondrial DNA is extracted from the mitochondria by digesting the mitochondrial membrane for 3 hours at 50° C. with 10 mg/ml proteinase K in 100 mM NaCl, 10 mM EDTA, 50 mM Tris-HCl, pH 7.4 and 1% SDS. The mitochondrial DNA is further extracted with phenol and chloroform and precipitated with ethanol.

The mitochondrial DNA isolated from the lymphocytes of a maternally genetically related donor is screened for "normalcy" using complete sequence analysis of the mitochondrial genome (see, e.g., Choo-Kang et al. *Diabetes* 51:2317-2320 (2002), which is incorporated herein by reference). Briefly, 28 to 30 overlapping primers evenly spaced along the mitochondrial DNA template are used for polymerase chain reaction (PCR) amplification across the entire 16-17 kilobase mitochondrial DNA genome. The overlapping PCR fragments are sequenced using an ABI Prism 377 DNA Sequencer (from Applied Biosystems, Foster City, Calif.). The resulting sequence is compared pair-wise using the BLAST2 sequence alignment tool and reference or wild-type sequence information contained in the National Center for Biotechnology Information (NCBI) databases and/or the MITOMAP database (see e.g. Altschul, et al. *J. Mol. Biol.* 215:403-410 (1990); Ruiz-Pesini et al. *Nucleic Acids Res.* 35:D823-D828 (2007), each of which is incorporated herein by reference).

The complete mitochondrial DNA sequences of a number of mammalian species including human, mouse, rat, dog, cat, cow, sheep and horse are available in the NCBI databases. In addition, specific information regarding polymorphisms and mutations of the human mitochondrial genome can be accessed through the MITOMAP database.

Myoblast cells for autologous transplantation are derived from skeletal muscle biopsy samples taken from the subject with heart failure (see, e.g. Dib, et al. *Circulation* 112:1748-1755 (2005), which is incorporated herein by reference). The skeletal muscle biopsy sample is trimmed of connective tissue, minced into a slurry, and digested at 37° C. with trypsin/EDTA (0.5 mg/ml trypsin, 0.53 mmol/L EDTA) and collagenase (0.5 mg/ml) to release the myoblast cells. The myoblast cells are plated and grown in myoblast basal growth medium (SkBM Basal Medium, Lonza, Basel Switzerland), containing 15% fetal bovine serum, recombinant human epidermal growth factor (10 ng/ml), and dexamethasone (3.9 ug/ml). The myoblast cells are expanded for 11 to 13 doublings prior to harvest.

Mitochondrial DNA is introduced into the myoblast cells using protein-mediated transfection (see, e.g., Keeney, et al. *Hum. Gene Ther.*, Abstract; 20:897-907 (2009), which is incorporated herein by reference). Briefly, the mitochondrial DNA isolated from the mitochondria of the maternally genetically related cells is combined with recombinant fusion protein complex containing mitochondrial transcription factor A (TFAM) engineered to include an N-terminal, 11-arginine protein transduction domain followed by a mitochondrial localization signal (MTD). The recombinant MDT-TFAM protein complex binds the donor mitochondrial DNA and is used to selectively import the DNA into the mitochondria of the myoblast cells. MDT-TFAM is combined in 2 to 3 fold excess with the donor mitochondrial DNA in a buffer designed to stabilize long DNA templates such as, for example, 85 mM potassium acetate, 25 mM Tricine (pH 8.7), 8% glycerol, 1% DMS) and 1.1 mM magnesium acetate and incubated for 30 minutes at 37° C. The MDT-TFAM-mitochondrial DNA solution is diluted in the myoblast basal growth medium described above and applied to the myoblast cells for 4 hours at 37° C.

Alternatively, the donor mitochondrial DNA can be introduced into the mitochondria of the myoblast cells using a mitochondrial leader sequence peptide that is recognized by the mitochondrial protein import machinery. For example, the mitochondrial DNA can be linked to the pre-sequence peptide of the nucleus encoded cytochrome c oxidase (COX) subunit VIII, (U.S. Patent Application 2004/0192627 A1, which is incorporated herein by reference). The mitochondrial DNA is conjugated to the pre-sequence peptide using pGeneGRIP™-PNA dependent chemistry (from, e.g., Genlantis, San Diego, Calif.). The PNA is designed to hybridize with a portion of the mitochondrial DNA as well as the pre-sequence peptide of COX subunit VIII. In this manner, the pre-sequence peptide is linked to the mitochondrial DNA and can facilitate import of the DNA into the mitochondria.

The mitochondrial DNA is imported into myoblast cells that have been pretreated with a mitochondrial toxin as described in Example 1 to generate $\rho^0$ myoblast cells. Alternatively, the mitochondrial DNA is imported into untreated myoblast cells to dilute the endogenous dysfunctional mitochondrial DNA with healthy mitochondrial DNA.

For transplantation, the autologous myoblast cells modified with mitochondrial DNA from the maternally genetically related cells are injected into the infarcted area of the recipient's heart. One to four, doses of 1 to $30 \times 10^7$ cells are injected in 3 to 30 injections of 0.1 ml each in a non-overlapping pattern in the area of infarction on the epicardial surface. Transplantation of autologous myoblast cells modified with donor mitochondrial DNA can be performed during concurrent coronary artery bypass grafting (CABG) or left ventricular assist device (LVAD) implantation. See, e.g. Dib, et al. *Circulation* 112:1748-1755 (2005), which is incorporated herein by reference.

Example 3

Treatment of Cytoplasmic Male Sterility in *Zea mays* Using Mitochondria from Maternally Genetically Related Cells A method is described for treating cytoplasmic male sterility in *Zea mays* (maize) using mitochondria isolated from maternally genetically related cells. Cytoplasmic male sterility is characterized by the inability of an otherwise normal plant to develop functional anthers, pollen, or male gametes, resulting in total or partial male sterility. Cytoplasmic male sterility is associated with a variety of mitochondrial DNA arrangements arising from low frequency, illegitimate recombination, or nonhomologous end joining activity within the mitochondrial genome, resulting in aberrant open reading frames comprised of chimeric sequences. (See, e.g., Mackenzie & McIntosh, *Plant Cell*, 11:571-585, (1999); Kubo & Newton, *Mitochondrion*; Abstract; 8:5-14 (2008), each of which is incorporated herein by reference). In order to restore male fertility in a deficient genotype of *Zea mays*, mitochondria from maternally genetically related cells isolated from a genotype of *Zea mays* exhibiting normal fertility are introduced into developing *Zea mays* embryos.

Mitochondria for microinjection into *Zea mays* embryos are isolated from seedlings of a maternally genetically related genotype. Briefly, one hundred grams of seedlings are placed in a grinding buffer (e.g., 0.35 M sorbitol, 50 mM Tris pH 7.6, 5 mM EDTA, 0.2% bovine serum albumin, 1.0% polyvinylpropyline, 0.025% spermine, 0.025% spermidine, 0.125% betamercaptoethanol) and homogenized in a blender on high for 3×15 seconds. Homogenate is filtered through cheesecloth and centrifuged at 3,000×g for 10 minutes. The resulting supernatant is centrifuged at 16,000×g for 30 minutes. The pellet is gently resuspended in a wash buffer (e.g., 0.35 M sorbitol, 50 mM Tris pH 7.6, 0.1% bovine serum albumin) and recentrifuged at 16,000×g. The pellet is resuspended in wash buffer with the addition of 25 mM $MgCl_2$ and treated with 100 ug/ml DNase I for 30-60 minutes on ice to remove contaminating DNA of the nucleus. The suspension is centrifuged at 2,000×g and the resulting supernatant centrifuged at 16,000×g. The pellet is resuspended in wash buffer and overlayed onto a Percoll gradient and centrifuged at 12,000×g for 1 hour. The mitochondria are collected at the 23:40 interface, washed with buffer, and centrifuged at 20,000×g for 30 minutes. The pellet containing purified mitochondria is resuspended in wash buffer and either used immediately to extract DNA or RNA or it is frozen at −20° C. in a 1:1 mixture of wash buffer and 50% glycerol.

The mitochondrial DNA isolated from the maternally genetically related cells is isolated using a cesium gradient. Briefly, the mitochondria are resuspended in a lysis buffer (e.g., 1.0% Sarkosyl, 50 mM Tris pH 8.0, 25 mM EDTA, 10 mg/ml proteinase K) and digested at 37° C. for 1 hour. Cesium chloride (100% w/v) is dissolved into the digest and ethidium bromide added to 0.2 mg/ml. The solution is centrifuged at 55,000 rpm for 20 hours. An ethidium bromide stained band containing the mitochondrial DNA is removed and the DNA precipitated with ethanol.

The mitochondrial DNA from the maternally genetically related cells is assessed for "normalcy" using a shotgun sequencing approach (see, e.g., Allen, et al., *Genetics* 177: 1173-1192 (2007), which is incorporated herein by reference). The purified mitochondrial DNA is fragmented, ligated into a plasmid cloning vector and transfected into an *Escherichia coli* host strain (e.g., DH10B-T1) to generate a sequencing library. The fragments of mitochondrial DNA are isolated and sequenced using an ABI Prism 377 DNA Sequencer (from Applied Biosystems, Foster City, Calif.). Sequence associated with the plasmid cloning vector is subtracted and over-lapping mitochondrial DNA sequences are pieced together to generate a complete mitochondrial genome sequence. The resulting mitochondrial genomic sequence from the maternally genetically related genotype is compared with that of other fertile strains of *Zea mays* (e.g., NA and NB) using a sequence alignment tool (e.g., Multalin; Corpet, *Nucl. Acids Res.*, 16:10881-10890, 1988, which is incorporated herein by reference).

Fertilized embryos for use in microinjection are isolated from *Zea mays* plants grown to maturity. Methods to isolate plant embryos are known in the art (see e.g., U.S. Pat. No. 6,300,543, which is incorporated herein by reference). Maize plants with silks 6-10 cm in length are pollinated by hand and the plants are placed in a growth chamber for at least 16 hours to allow fertilization to occur. Ovaries are isolated by removing husks and silks from the cobs and cutting the cobs transversely in 3 cm segments. The segments are sterilized for 10 minutes in 70% ethanol and rinsed in deionized water. Ovaries are then removed and mounted for sectioning.

Specimen blocks for use in the microtome are surface sterilized in 70% ethanol for 10 minutes, and the alcohol is evaporated in a laminar flow hood. A thin layer of adhesive, "Quik Set 404" (available from Locktite Corp., Newington, Conn.), is used to immobilize the ovaries with their adiaxial surface up. The blocks with attached ovaries are placed in a Vibratome (available from Technical Products International.,  St. Louis, Mo.), and sectioned at a thickness of 200-400 μm. Microscopic inspection of the sections is used to identify 250 μm to 300 μm slices containing embryo sacs. Sections containing embryo sacs are collected and placed on a modified Murashige-Skoggs medium with 0.4 mg/L L-asparagine, 0.1 mg/L 6-benzylaminopurine (BAP) and 15% sucrose, pH 5.8. Media and culture conditions for plant embryos are known in the art (see e.g., Hecht et al., *Physiol. Plant* 127: 803-816 (2001), which is incorporated herein by reference).

Zygotes contained in intact embryo sacs are microinjected with the mitochondrial isolated from the maternally genetically related strain. For microinjection, one to six picoliters of solution containing 200-2000 mitochondria is microinjected into single oocytes using a Stemi SV11 Stereomicroscope (available from Carl Zeiss Microimaging, Inc., Thornwood, N.Y.) equipped with Narishige micromanipulators and a PL-100 pico-injector (micromanipulators and injector are available from Tritech Research, Los Angeles, Calif.). Embryo sacs are cultured at 25°C. in the dark on modified Murashige-Skoggs medium with 0.4 mg/L L-asparagine, 0.1 mg/L 6-benzylaminopurine (BAP) and 15% sucrose, pH 5.8.

In order to grow plants from the microinjected zygotes, the embryo sacs are transferred to media lacking BAP, and cultured in vitro. Embryo sacs are cultured in Murashige-Skoggs medium with 0.4 mg/L L-asparagine and 10% sucrose, pH 5.8 for 5 days at 25° C. in the dark, and then transferred to the same medium containing only 3% sucrose for another 5 days. When young shoots are approximately 1.5 cm long, they are exposed to light. After the embryos have grown into plantlets in vitro, they are planted in sterilized soil or vermiculite and grown to maturity in a greenhouse. The resulting plants are assessed for the presence of anthers, pollen and/or male gametes as indicators of recovery of male fertility. Various methods for determining viability of pollen and/or male gametes have been described (see, e.g., Dumas & Mogensen, *Plant Cell,* 5:1337-1348 (1993) which is incorporated herein by reference).

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of modifying a eukaryotic cell, comprising: providing at least one exogenous cellular component derived from a maternally genetically related cell, further comprising measuring the membrane potential of the eukaryotic cell or the maternally genetically related cell at least one of prior to, during, or subsequent to providing the at least one exogenous cellular component to the eukaryotic cell, wherein the exogenous cellular component is an exogenous mitochondria.

2. The method of claim 1, wherein at least one of the exogenous mitochondria, exogenous mitochondrial DNA, or exogenous cell nucleus, is provided to at least one intracellular compartment of the eukaryotic cell.

3. The method of claim 1, wherein at least one exogenous cellular component is provided in response to the presence or level of at least one eukaryotic cell indicator.

4. The method of claim 3, wherein the at least one eukaryotic cell indicator includes at least one indicator of one or more of a property of the eukaryotic cell; a property of administering the at least one mitochondria, mitochondrial DNA, or cell nucleus, to the eukaryotic cell; eukaryotic cell death; eukaryotic cell division; eukaryotic cell cytoskeletal rearrangement; eukaryotic cell mitochondrial quality, quantity, or arrangement; or eukaryotic cell or tissue secretion.

5. The method of claim 4, wherein the property of the eukaryotic cell includes at least one of eukaryotic cell size, eukaryotic cell stage, eukaryotic cell quality, health of the subject from which the eukaryotic cell originates, species of the subject from which the eukaryotic cell originates, immunological background of the eukaryotic cell, mitotic rate of the eukaryotic cell, metabolic profile of the eukaryotic cell, genomic profile of the eukaryotic cell, transcriptomic profile of the eukaryotic cell, or proteomic profile of the eukaryotic cell, or storage conditions of the eukaryotic cell.

6. The method of claim 5, wherein the storage conditions of the eukaryotic cell include at least one of duration of storage time, storage temperature, storage size, eukaryotic cell dilution, or storage solution(s).

7. The method of claim 1, further comprising selecting the eukaryotic cell for further manipulation.

8. A method of modifying a eukaryotic cell, comprising: providing at least one exogenous cellular component derived from a maternally genetically related cell, further comprising measuring the membrane potential of the eukaryotic cell or the maternally genetically related cell at least one of prior to, during, or subsequent to providing the at least one exogenous cellular component to the eukaryotic cell, wherein the maternally genetically related cell is derived from the child of the source of the eukaryotic cell, wherein the source of the eukaryotic cell is female, and wherein the exogenous cellular component is an exogenous mitochondria.

9. The method of claim 8, wherein the maternally genetically related cell includes or is derived from at least one of an oocyte, or stem cell from the child of the source of the eukaryotic cell.

10. A method of modifying a eukaryotic cell, comprising: providing at least one exogenous cellular component derived from a maternally genetically related cell, further comprising measuring the membrane potential of the eukaryotic cell or the maternally genetically related cell at least one of prior to, during, or subsequent to providing the at least one exogenous cellular component to the eukaryotic cell, wherein the source of the exogenous cellular component is of chronologically younger age than the source of the eukaryotic cell, wherein the exogenous cellular component is an exogenous mitochondria.

* * * * *

UNITED STATES PATENT AND TRADEMARK OFFICE
CERTIFICATE OF CORRECTION

Page 1 of 1

PATENT NO. : 8,338,178 B2
APPLICATION NO. : 12/925849
DATED : December 25, 2012
INVENTOR(S) : Roderick A. Hyde and Lowell L. Wood, Jr.

It is certified that error appears in the above-identified patent and that said Letters Patent is hereby corrected as shown below:

In the Claims

Column 24, line 53, claim 2

"wherein at least one of the exogenous mitochondria, exogenous mitochondrial DNA, or exogenous cell nucleus," should read --wherein the exogenous mitochondria--

Signed and Sealed this
Tenth Day of June, 2014

Michelle K. Lee
*Deputy Director of the United States Patent and Trademark Office*